(12) United States Patent
Fowler et al.

(10) Patent No.: US 11,510,485 B2
(45) Date of Patent: Nov. 29, 2022

(54) ORAL CARE SYSTEM

(71) Applicant: Sage Products, LLC, Cary, IL (US)

(72) Inventors: Paul Michael Fowler, Rockford, IL (US); Ronald Christopher Cagle, Crystal Lake, IL (US); Theresa L. Sebastian, Cary, IL (US); Daniel R. Ulreich, Cary, IL (US); Jodi Marie Balbinot, Cary, IL (US); Kristin Marie Sexton, Lake in the Hills, IL (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 17/713,392

(22) Filed: Apr. 5, 2022

(65) Prior Publication Data

US 2022/0225757 A1     Jul. 21, 2022

Related U.S. Application Data

(63) Continuation of application No. 17/008,245, filed on Aug. 31, 2020, now Pat. No. 11,291,295, which is a
(Continued)

(51) Int. Cl.
    *B65D 81/24*        (2006.01)
    *A46B 15/00*      (2006.01)
    (Continued)

(52) U.S. Cl.
    CPC ............ *A46B 15/0061* (2013.01); *A46B 5/02* (2013.01); *A46B 9/005* (2013.01); *A46B 9/04* (2013.01);
(Continued)

(58) Field of Classification Search
    CPC .......... B44D 3/125; A61C 17/08; A47K 1/09; A61L 2/18; A61L 2/26; A61L 2202/121;
(Continued)

(56) References Cited

U.S. PATENT DOCUMENTS

| | | | |
|---|---|---|---|
| 1,128,045 A | 2/1915 | Reenstierna | |
| 1,254,714 A | 1/1918 | Mccombs | |

(Continued)

FOREIGN PATENT DOCUMENTS

| | | | |
|---|---|---|---|
| CN | 203493048 U | 3/2014 | |
| FR | 2606615 A | 5/1988 | |

(Continued)

OTHER PUBLICATIONS

International Search Report and Written Opinion for International Application No. PCT/US2017/061633, dated Apr. 6, 2018, 17 pages.
(Continued)

*Primary Examiner* — Luan K Bui
(74) *Attorney, Agent, or Firm* — Foley & Lardner LLP

(57) ABSTRACT

The present disclosure generally relates to oral care systems and devices. An oral care system includes a container defining an interior portion. The container includes a repository provided within the interior portion and configured to hold a fluid, and a barrier configured to maintain the fluid separate from the interior portion. The barrier is configured to be breached to expose the interior portion to the fluid. The system further includes a tube configured to slide in the interior portion of the container. The tube includes a distal end configured to breach the barrier when the tube is moved in a direction of the fluid in the repository.

14 Claims, 31 Drawing Sheets

Related U.S. Application Data continuation of application No. 15/813,051, filed on Nov. 14, 2017, now Pat. No. 10,758,034.

(60) Provisional application No. 62/421,911, filed on Nov. 14, 2016, provisional application No. 62/457,708, filed on Feb. 10, 2017, provisional application No. 62/519,049, filed on Jun. 13, 2017.

(51) Int. Cl.

| | |
|---|---|
| *A61C 17/08* | (2006.01) |
| *A46B 9/00* | (2006.01) |
| *A46B 17/06* | (2006.01) |
| *A46B 11/00* | (2006.01) |
| *A46B 5/02* | (2006.01) |
| *A46B 9/04* | (2006.01) |
| *A61L 2/18* | (2006.01) |
| *A61L 2/26* | (2006.01) |
| *A47K 1/09* | (2006.01) |

(52) U.S. Cl.
CPC ...... *A46B 11/0003* (2013.01); *A46B 15/0053* (2013.01); *A46B 15/0081* (2013.01); *A46B 17/06* (2013.01); *A61C 17/08* (2019.05); *A46B 2200/1066* (2013.01); *A47K 1/09* (2013.01); *A61L 2/18* (2013.01); *A61L 2/26* (2013.01); *A61L 2202/121* (2013.01)

(58) Field of Classification Search
CPC .. A46B 5/02; A46B 9/005; A46B 9/04; A46B 11/0003; A46B 15/0053; A46B 15/0061; A46B 15/0081; A46B 17/06; A46B 2200/1066
USPC ....... 206/15.2, 15.3, 209, 361, 362.2, 362.3, 206/581; 53/428; 132/308
See application file for complete search history.

(56) References Cited

U.S. PATENT DOCUMENTS

| | | |
|---|---|---|
| 1,283,403 A | 10/1918 | Eustis |
| 1,419,593 A | 6/1922 | Thompson |
| D149,620 S | 5/1948 | Darr |
| D162,881 S | 4/1951 | Richardson |
| D172,862 S | 8/1954 | Brennan |
| D174,292 S | 3/1955 | Perez |
| 2,782,909 A * | 2/1957 | Mcnamara ............ B44D 3/125 220/802 |
| D186,902 S | 12/1959 | Fried |
| 3,411,723 A | 11/1968 | Kohn |
| 3,488,788 A | 1/1970 | Robinson |
| 3,840,932 A | 10/1974 | Balamuth et al. |
| 4,149,815 A | 4/1979 | Kawam |
| 4,167,228 A | 9/1979 | Cheetham |
| 4,174,035 A | 11/1979 | Wiegner |
| 4,192,035 A | 3/1980 | Kuris |
| 4,195,731 A | 4/1980 | Cavazza |
| 4,214,657 A * | 7/1980 | Winston ............... A47K 1/09 206/362.1 |
| 4,317,605 A * | 3/1982 | Alissandratos ........ A47K 11/10 312/305 |
| D282,317 S | 1/1986 | Herzfeld |
| D282,319 S | 1/1986 | Herzfeld |
| D282,698 S | 2/1986 | Newton, Jr. |
| 4,570,652 A * | 2/1986 | Chavez ............... A61L 2/18 206/362.2 |
| 4,854,760 A | 8/1989 | Unidec |
| 4,915,219 A * | 4/1990 | Ottimo ............... A01N 25/34 206/362.1 |
| 4,976,379 A | 12/1990 | Sloan |
| 4,995,509 A | 2/1991 | Kornfeind |
| 5,022,559 A | 6/1991 | Condon |
| 5,246,046 A | 9/1993 | Schramm |
| 5,311,632 A | 5/1994 | Center |
| 5,495,876 A | 3/1996 | Schramm |
| 5,501,340 A | 3/1996 | Stafford |
| D377,867 S | 2/1997 | Berghash et al. |
| RE36,131 E | 3/1999 | Schramm |
| 5,908,057 A | 6/1999 | Schramm |
| 6,082,999 A | 7/2000 | Tcherny et al. |
| 6,243,906 B1 | 6/2001 | Holliday et al. |
| 6,280,112 B1 | 8/2001 | Vieu |
| D453,888 S | 2/2002 | Gottwald |
| 6,397,859 B1 | 6/2002 | Byrd |
| 6,418,940 B1 | 7/2002 | Tcherny et al. |
| D470,661 S | 2/2003 | Zetsche |
| 6,530,707 B1 | 3/2003 | Byrne et al. |
| 6,595,822 B1 | 7/2003 | Thai |
| 6,638,131 B1 | 10/2003 | Thai |
| 6,669,475 B2 | 12/2003 | Kandelman et al. |
| 6,702,113 B2 | 3/2004 | Marino |
| 6,704,965 B2 | 3/2004 | Ale et al. |
| D499,811 S | 12/2004 | Nan |
| 6,857,928 B2 | 2/2005 | Thai |
| RE39,443 E | 12/2006 | Schramm |
| 7,244,161 B2 | 7/2007 | Thai |
| D563,069 S | 2/2008 | Yovanovich |
| 7,399,133 B1 | 7/2008 | Eversole |
| D576,799 S | 9/2008 | Vezin et al. |
| D576,801 S | 9/2008 | Dretzka |
| 7,524,230 B2 | 4/2009 | Thai |
| D592,404 S | 5/2009 | Toefferl et al. |
| 7,967,519 B2 | 6/2011 | Gueret |
| RE42,610 E | 8/2011 | Schramm |
| D669,981 S | 10/2012 | Ruiz et al. |
| 8,506,192 B2 | 8/2013 | Allbritton |
| 8,632,268 B2 | 1/2014 | Kemp |
| D709,713 S | 7/2014 | Yang et al. |
| D720,137 S | 12/2014 | Schuler |
| 8,932,522 B2 | 1/2015 | Duncan |
| D736,907 S | 8/2015 | Mccracken et al. |
| D741,068 S | 10/2015 | Frazier |
| D749,919 S | 2/2016 | Cianciolo |
| D751,688 S | 3/2016 | Daly |
| D752,882 S | 4/2016 | Chang |
| D774,775 S | 12/2016 | Buchholz |
| D776,534 S | 1/2017 | Stratton |
| D784,024 S | 4/2017 | Jun |
| D792,214 S | 7/2017 | Kerill et al. |
| 9,810,575 B2 | 11/2017 | Lance |
| D804,770 S | 12/2017 | Zoubovsky |
| D808,431 S | 1/2018 | Tseng |
| D808,660 S | 1/2018 | Kresge |
| D812,913 S | 3/2018 | Way |
| D825,885 S | 8/2018 | Falcone |
| D825,932 S | 8/2018 | Jun |
| D828,082 S | 9/2018 | Ramos |
| D835,383 S | 12/2018 | Petersen |
| D860,654 S | 9/2019 | Bram et al. |
| D862,087 S | 10/2019 | Ma |
| D864,576 S | 10/2019 | Cagle et al. |
| D874,153 S | 2/2020 | Fowler et al. |
| 10,717,020 B2 | 7/2020 | Schramm |
| D912,990 S | 3/2021 | Cagle et al. |
| D918,591 S | 5/2021 | Serval et al. |
| 2001/0035413 A1 | 11/2001 | Thai |
| 2002/0138931 A1 | 10/2002 | Davies |
| 2004/0129580 A1 | 7/2004 | Cochran et al. |
| 2004/0211683 A1 | 10/2004 | Barham et al. |
| 2006/0225839 A1* | 10/2006 | Mays ................ A46B 15/0095 156/325 |
| 2006/0289316 A1 | 12/2006 | Henry |
| 2007/0277339 A1 | 12/2007 | Barsheshet |
| 2008/0245681 A1 | 10/2008 | Healis |
| 2013/0074867 A1 | 3/2013 | Leung |
| 2013/0112591 A1* | 5/2013 | Allbritton ......... A46B 11/0044 132/308 |
| 2014/0137352 A1 | 5/2014 | Golla et al. |
| 2017/0311707 A1 | 11/2017 | Beck et al. |
| 2018/0055184 A1 | 3/2018 | Mcveigh et al. |
| 2018/0055187 A1 | 3/2018 | Galligan |

(56) References Cited

U.S. PATENT DOCUMENTS

| | | |
|---|---|---|
| 2018/0132605 A1 | 5/2018 | Fowler et al. |
| 2018/0289145 A1 | 10/2018 | Cagle et al. |
| 2020/0390230 A1 | 12/2020 | Fowler et al. |

FOREIGN PATENT DOCUMENTS

| | | |
|---|---|---|
| JP | 2013-516207 | 5/2013 |
| WO | WO-2009/138723 | 11/2009 |

OTHER PUBLICATIONS

Partial International Search Report for International Application No. PCT/US2017/061633, dated Feb. 12, 2018, 12 pages.

Sage Products | Oral Hygiene Systems for Non-Ventilated Patients, posted on Jan. 31, 2009, (C) Sage Products LLC 2020 [online], [site visited Aug. 31, 2020]. Available from Internet, <URL: https://sageproducts.com/oral-hygiene-for-non-ventilated-patients/>.

Stryker Sage Self Oral Care. Toothbrush with Corinz Antiseptic Cleansing and Moisturizing Oral Rinse, published Dec. 13, 2019, https://web.archive.org/web/20191213200952/https://www.stryker.com/us/en/sage/roducts/sage-self-oral-care.html, 5 pages.

YouTube | Sage Self Oral Care Training, published on Oct. 23, 2019 by Stryker Sage, (c) 2020 YouTube, LLC, [online], [site visited Aug. 31, 2020]. Available from Internet, [frames 0:19-0:22] <URL: https://www.youtube.com/watch?v=SDpc3lqxpOc&feature=youtu.be/>.

\* cited by examiner

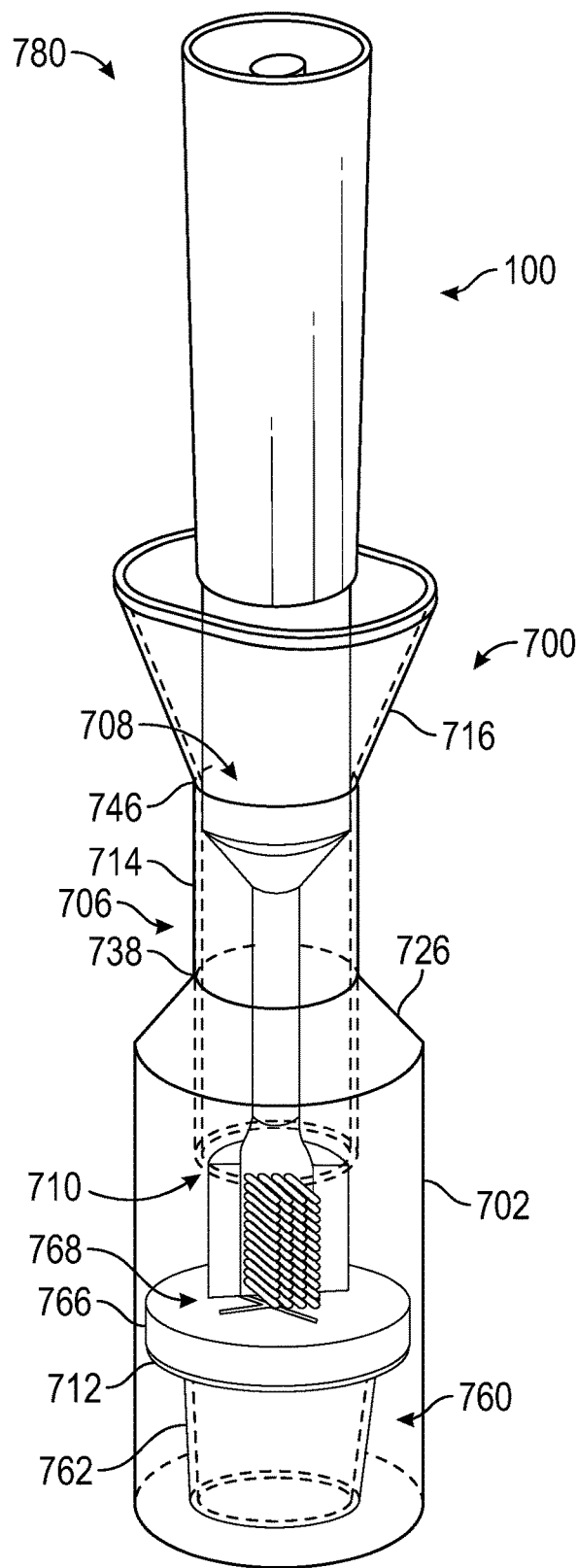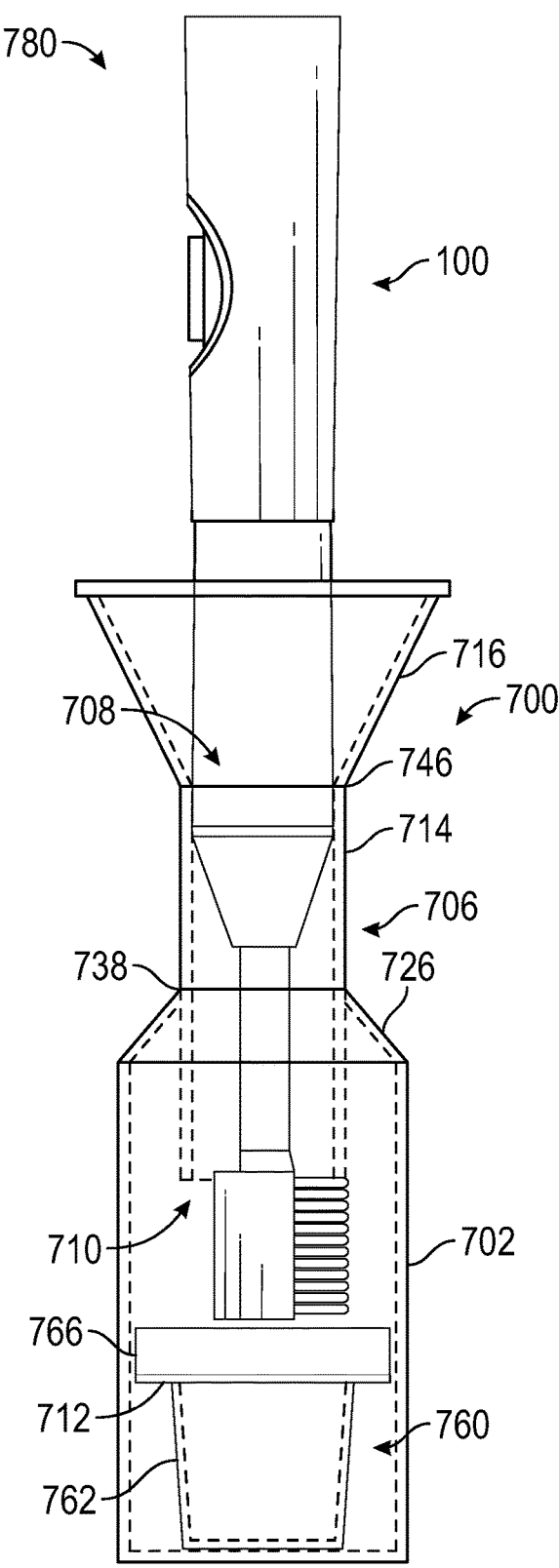
FIG. 10A  FIG. 10B

ORAL CARE SYSTEM

CROSS-REFERENCE TO RELATED PATENT APPLICATIONS

This application is a continuation of U.S. patent application Ser. No. 17/008,245, filed Aug. 31, 2020, which is a continuation of U.S. patent application Ser. No. 15/813,051, filed Nov. 14, 2017; U.S. patent application Ser. No. 15/813,051 claims priority to U.S. Provisional Patent Application No. 62/421,911, filed on Nov. 14, 2016, U.S. Provisional Patent Application No. 62/457,708, filed on Feb. 10, 2017, and U.S. Provisional Patent Application No. 62/519,049, filed on Jun. 13, 2017; each of which is hereby incorporated by reference in its entirety.

BACKGROUND

Standard toothbrush designs are not ideal for use in hospitals or other medical treatment facilities where patients may have compromised immune systems. In these settings, there is an increased risk of, for example, contracting pneumonia. Accordingly, compliance to a proper oral care regimen, which includes brushing three to four times per day, is important.

Due to its repeated reuse, use of a standard toothbrush creates a risk of bacterial infection. Additionally, standard toothbrushes are also not suitable for some patients because patients may be unable to spit or otherwise voluntarily remove liquids from their mouths, may not have easy access to water, or may have difficulty holding and using a toothbrush having the standard size and shape. Standard toothpaste may also be unsuitable for use by such patients, and it may be difficult for such patients to find and apply the proper amount of toothpaste to a toothbrush.

In many circumstances, medical procedures like oral care must be repeated multiple times. For example, in oral care, a series of mouth care products must be used in a repetitious fashion, such as for periodic cleaning sessions, where there can be evacuation, brushing of the teeth, and swabbing of the mouth and gums. With the repetition of each procedure occurring after a predetermined interval, such as every few hours, it may be cumbersome for the medical care professional or the patient to gather the necessary instrument(s) repeatedly throughout the day.

BRIEF DESCRIPTION OF THE DRAWINGS

The following disclosure as a whole may be best understood by reference to the provided detailed description when read in conjunction with the accompanying drawings.

FIGS. 10A and 10B are schematic side views of an oral care system, according to another exemplary embodiment.

DETAILED DESCRIPTION

Figure 1:
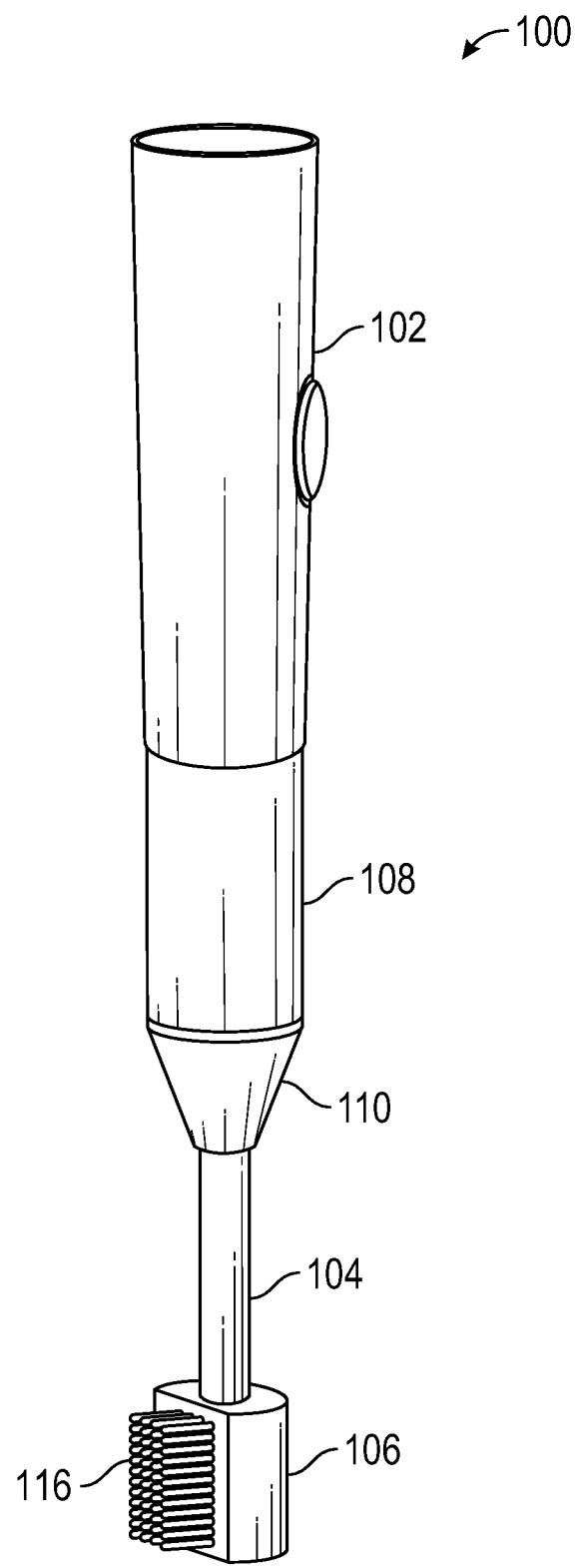
FIG. 1 is a side perspective view of an oral care device, according to an exemplary embodiment.
Figure 2:
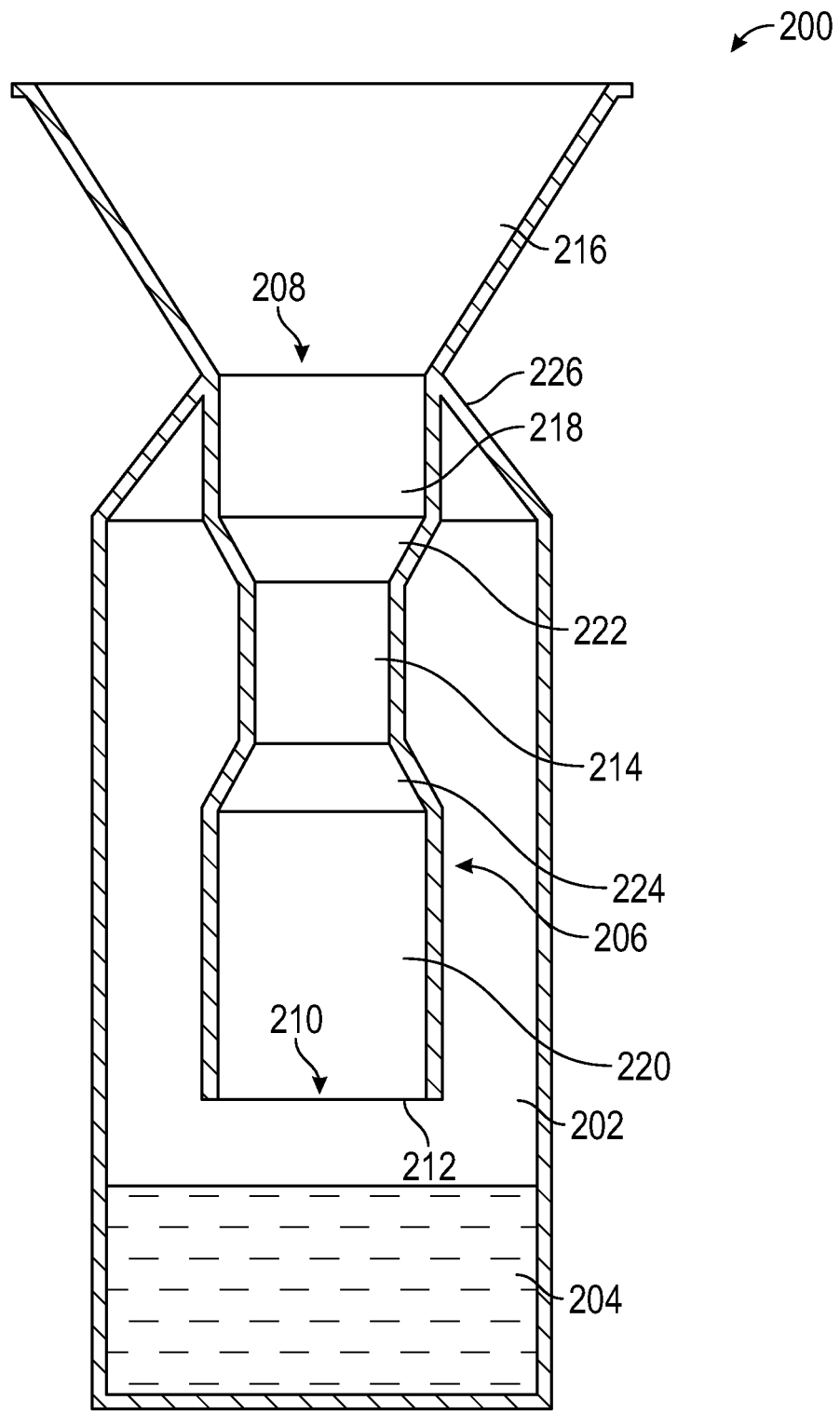
FIG. 2 is a sectional view of a unit dose oral fluid container, according to an exemplary embodiment.

According to various described embodiments, an oral care product that improves compliance with an oral care plan by providing all necessary tools and accessories for completing the plan without requiring significant effort from a patient or health care provider. According to various exemplary embodiments, an oral care system for use in a hospital setting includes an oral care device (e.g., a toothbrush as shown in FIG. 1) and a unit dose oral fluid container (e.g., as shown in FIG. 2). The oral care device and/or oral care system may be intended for single use. Various embodiments of an oral care systems are described in further detail below.

Referring first to FIG. 1, a side perspective view of an oral care device, such as toothbrush 100 is shown, according to an exemplary embodiment. The toothbrush 100 includes a handle 102 coupled to a stem 104, which in turn is coupled to a head 106. The head 106 includes bristles 116 used to clean a patient's teeth. In some embodiments, the toothbrush 100 also includes supports 108 and 110 between the handle 102 and the stem 104 to provide length and stability to the toothbrush 100. Further, in certain embodiments, the toothbrush 100 includes a suction mechanism. In such embodiments, the supports 108 and 110 house components of the suction mechanism. Suction is then provided by a device external to the toothbrush 100 and connected by tubing to the toothbrush 100. Once the suction device external to the toothbrush 100 is activated, the patient may initiate suction at the head 106 of the toothbrush 100. For example, the patient may cover a hole located on the handle 102 or press a button on the toothbrush 100 to provide suction.

Referring now to FIG. 2, a sectional view of a unit dose oral fluid container 200 is shown, according to an exemplary embodiment. In certain embodiments, the oral fluid is an antiseptic fluid. The oral fluid container 200 defines a receptacle 202 in the interior of the oral fluid container 200. The receptacle 202 is sized and configured to provide a stable base for the oral fluid container 200. The receptacle 202 is also configured to serve as a repository and hold a volume of oral fluid 204, such as an antiseptic fluid. In some embodiments, the receptacle 202 is configured to hold between 9.0 mL and 10.0 mL of oral fluid 204, and in certain embodiments, the receptacle 202 is configured to hold 9.5 mL of oral fluid 204. The receptacle 202 portion of the oral fluid container 200 may be cylindrical, though the receptacle 202 may have a different shape in various embodiments. A top portion of the oral fluid container 200 also includes a funnel 216 (e.g., a projection having a mouth and a base, where the projection narrows from the mouth to the base, where the base is proximate the oral fluid 204, and where the mouth comprises a shape that may be a circle, oval, square, rectangle, etc.), and an internal chamber 206 also within the interior of the oral fluid container 200 provides a channel between the receptacle 202 and the funnel 216. In various arrangements, the receptacle 202 is coupled to the funnel 216 via a conical expansion region 226 (e.g., shaped like an inverted funnel).

The internal chamber 206 has an hourglass shape and includes an inlet 208 and an outlet 210. The inlet 208 provides a connection between the funnel 216 and the internal chamber 206. The outlet 210 provides a connection between the internal chamber 206 and the receptacle 202. The inlet 208 is defined by a first chamber 218 that is coupled to the funnel 216. A second funnel portion 222 couples the first chamber 218 to a neck portion 214, which has a reduced diameter relative to the first chamber 218 and a second chamber 220. The outlet 210 is defined by the second chamber 220. The second chamber 220 is coupled to the neck portion 214 via an inverted funnel portion 224. Additionally, the outlet 210 includes a penetrable barrier that the toothbrush 100 must pass through for use of the oral fluid container. For example, in some embodiments, the outlet 210 is covered by a seal 212 prior to use. Alternatively, in other embodiments, the outlet 210 is covered by a septum (e.g., as described below with reference to FIGS. 5A-5C), a cover with a cross cut (e.g., similar to foam cover 666 or sponge cover 766 described below with reference to FIG. 9 and FIGS. 10A and 10B, respectively). The internal chamber 206, and particularly second chamber 220, provides a housing for the toothbrush 100 of FIG. 2A while not in use (e.g., as shown in FIG. 6A).

The neck portion 214, which has a reduced diameter relative to the first chamber 218 and second chamber 220, is configured to remove excess oral fluid 204 from the toothbrush 100 as the toothbrush is removed from the internal chamber 206 for use (e.g., because, in the embodiment shown, the reduced diameter of the neck portion 214 presses out excess oral fluid 204 from the toothbrush 100 through a squeezing effect). The internal chamber 206 also facilitates passage of saliva and oral fluid waste that has been spit or expelled by the patient (hereinafter "brushing waste"), from the funnel 216 to the receptacle 202 during or after the use of the toothbrush 100 by the patient. The funnel 216 provides a larger target area for a patient to deposit the brushing waste while brushing to minimize the mess associated with spitting the used oral fluid into the receptacle 202.

In some embodiments, the oral fluid container 200 is manufactured using an injection mold. In other embodiments, rather than forming the neck portion 214 using injection molding, a separate element is placed inside the internal chamber 206 after injection molding to create a neck portion 214 having a reduced diameter. In still other embodiments, rather than forming the second funnel portion 222, the neck portion 214, and the inverted funnel portion 224 using injection molding along with the rest of the oral fluid container 200, a separate element is placed inside the internal chamber 206 after injection molding of the rest of the oral fluid container 200 to create the second funnel portion 222, the inverted funnel portion 224, and the neck portion 214. Additionally, in various embodiments, the oral fluid container 200 is configured to be symmetrical around an axis extending through a center of the oral fluid container 200.

Figure 3:
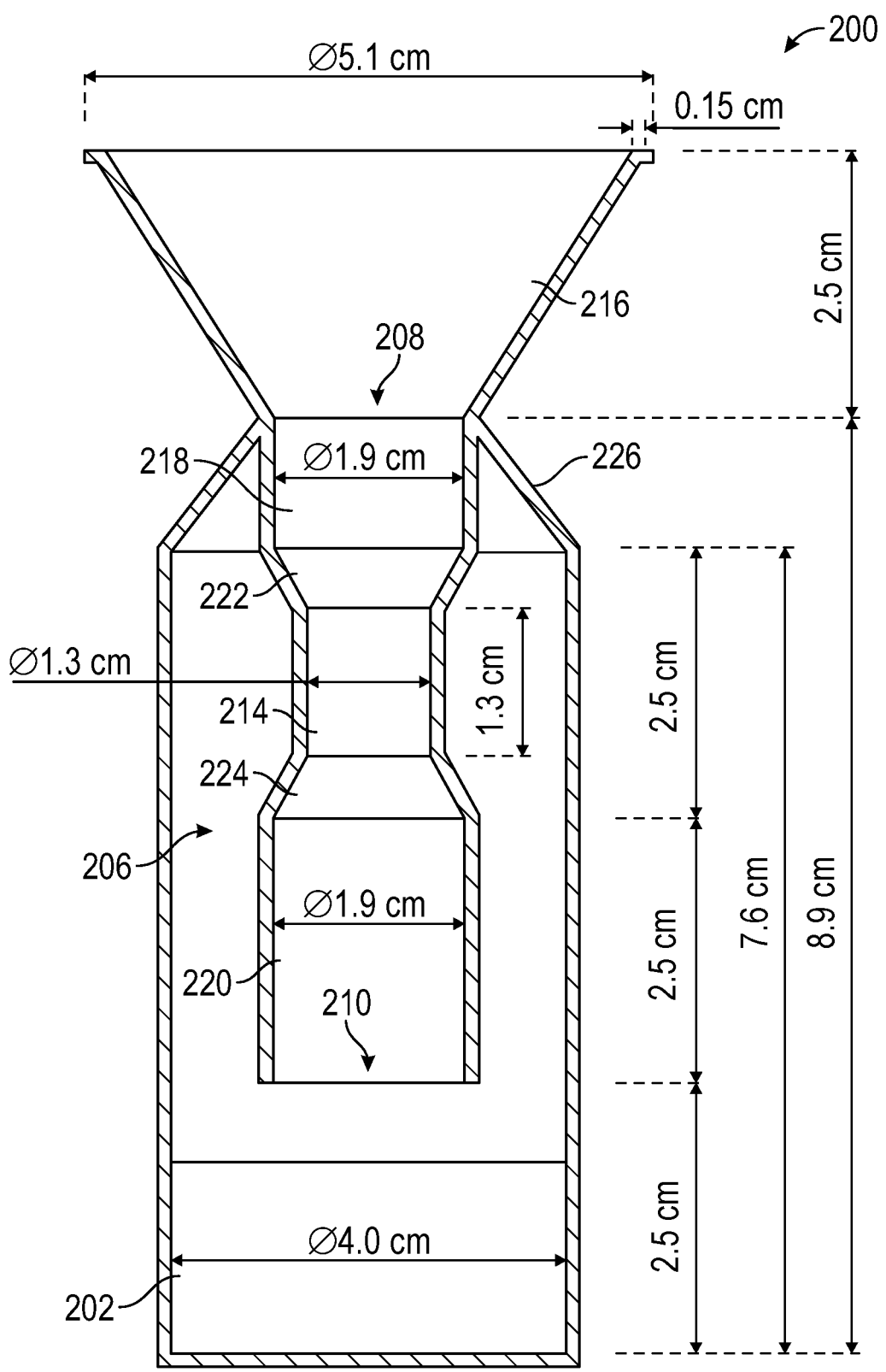
FIG. 3 is a sectional view of the unit dose oral fluid container of FIG. 2 with dimensions, according to an example embodiment.

In various embodiments, the unit dose oral fluid container 200 is designed to be spill-resistant. As such, in various arrangements, the unit dose oral fluid container 200 is designed with specific, spill-resistant dimensions. FIG. 3 is a sectional view of the unit dose oral fluid container of FIG. 2 with such dimensions, according to an exemplary embodiment. In the embodiment of FIG. 3, the oral fluid container 200 altogether has a total height of 11.4 cm (4.5 inches). From the base of the exemplary receptacle 202 to the base of the funnel 216, the receptacle 202 is 8.9 cm (3.5 inches) tall, and the portion of the receptacle 202 with a constant diameter (i.e., not including the conical expansion region 226) is 7.6 cm (3.0 inches) tall and has a diameter of 4.0 cm (1.5 inches). The funnel 216 has a height of 2.5 cm (1.0 inches) and an upper diameter of 5.1 cm (2.0 inches). The inlet 208 of the internal chamber 206, and the first chamber 218 that defines the inlet 208, has a diameter of 1.9 cm (0.75 inches). The outlet 210, and the second chamber 220 that defines the outlet, also has a diameter of 1.9 cm (0.75 inches), and the outlet 210 ends 2.5 cm (1.0 inches) above the base of the receptacle 202. The first chamber 218 is 1.3 cm (0.5 inches) tall, and the second chamber 220 is 2.5 cm (1.0 inches) tall. The neck portion 214 has a height of 1.3 cm (0.5 inches) and a diameter of 1.3 cm (0.5 inches). The second funnel portion 222, the neck portion 214, and the inverted funnel portion 224 have a combined height of 2.5 cm (1.0 inches). Overall, the oral fluid container 200 has a wall width of 0.15 cm (0.06 inches). With such dimensions, the oral fluid container 200 is spill-resistant up to 15 mL to accommodate for a volume of both unused oral fluid and the saliva and oral fluid brushing waste (e.g., after use of the toothbrush 100).

Further referring to FIG. 3, it should be understood that other dimensions may also be used to achieve the same or substantially the same ratios and configurations as those described above. Such dimension ratios allow the oral fluid container 200 to maintain its spill-resistant properties.

Figure 4C:
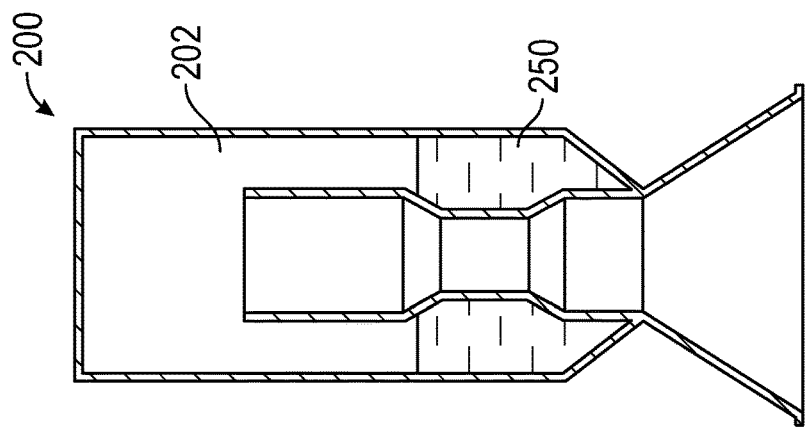
FIGS. 4A-4C are sectional views of the unit dose oral fluid container of FIG. 2 in various orientations, according to an exemplary embodiment.
Figure 4B:
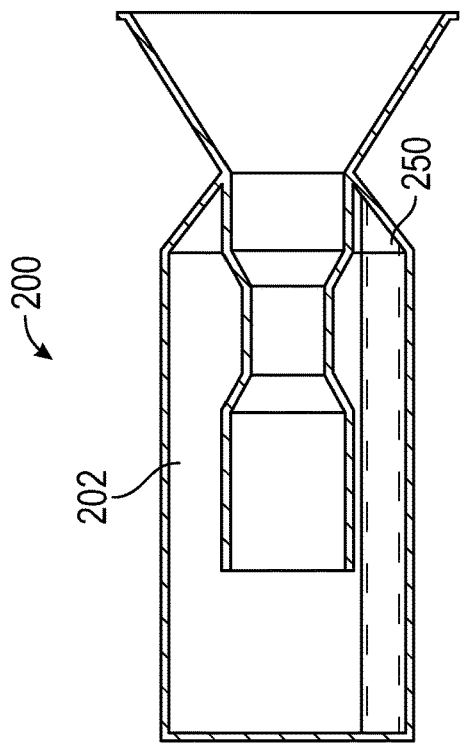
Figure 4A:
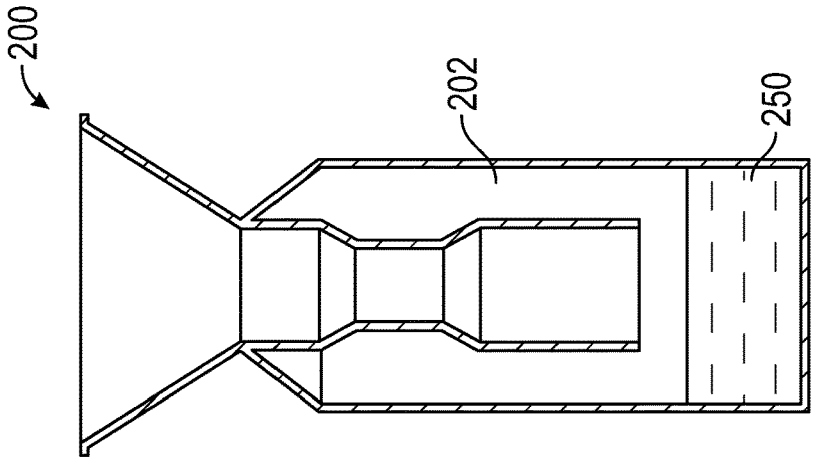

Referring now to FIGS. 4A-4C, schematic views of the unit dose oral fluid container 200 in various orientations that illustrate spill-resistant features of the oral fluid container 200 are shown, according to an exemplary embodiment. FIG. 4A shows the oral fluid container 200 in an upright position with a combination 250 of unused oral fluid and brushing waste (e.g., after use of the toothbrush 100), though the oral fluid container 200 could alternatively be filled with just oral fluid 204 (e.g., before use of the toothbrush 100). FIG. 4B shows the oral fluid container 200 in a horizontal position with the combination 250 of unused oral fluid and brushing waste. As shown, the combination 250 of unused oral fluid and brushing waste does not exit the oral fluid container 200 through the internal chamber 206 when the oral fluid container 200 is in the horizontal position but is instead maintained within the receptacle 202. FIG. 4C shows the oral fluid container 200 in an upside-down orientation. As shown, the combination 250 of unused oral fluid and brushing waste does not leave the oral fluid container 200 but is again maintained within the receptacle 202.

Figure 5A:
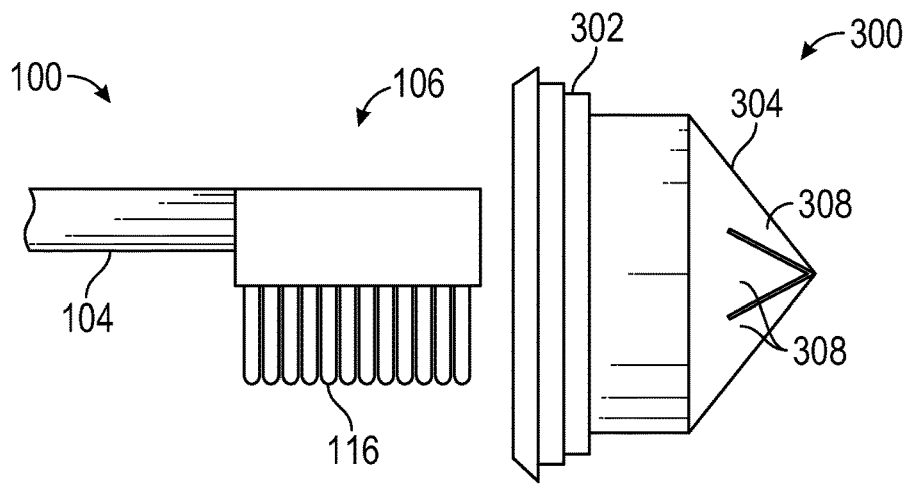
FIGS. 5A-5C are side views of a septum that may be included in the unit dose oral fluid container of FIG. 2, according to an exemplary embodiment.
Figure 5B:
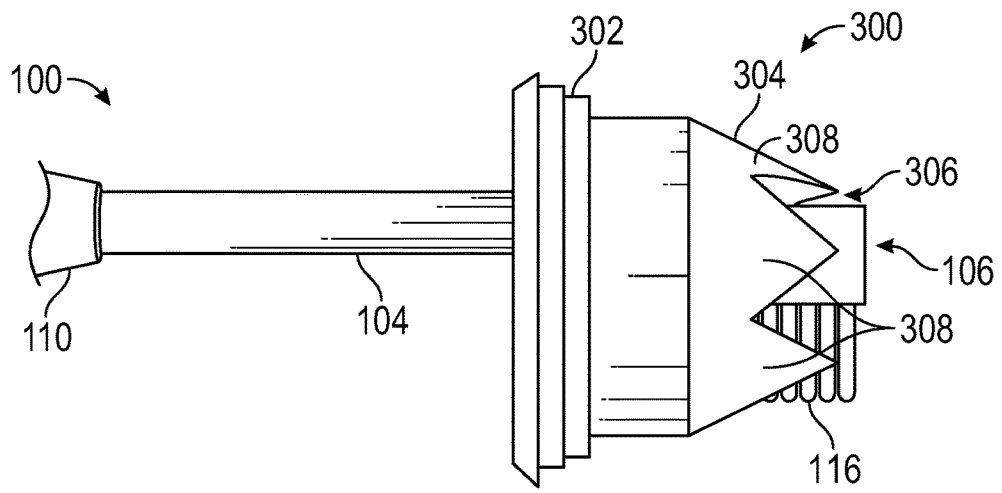
Figure 5C:
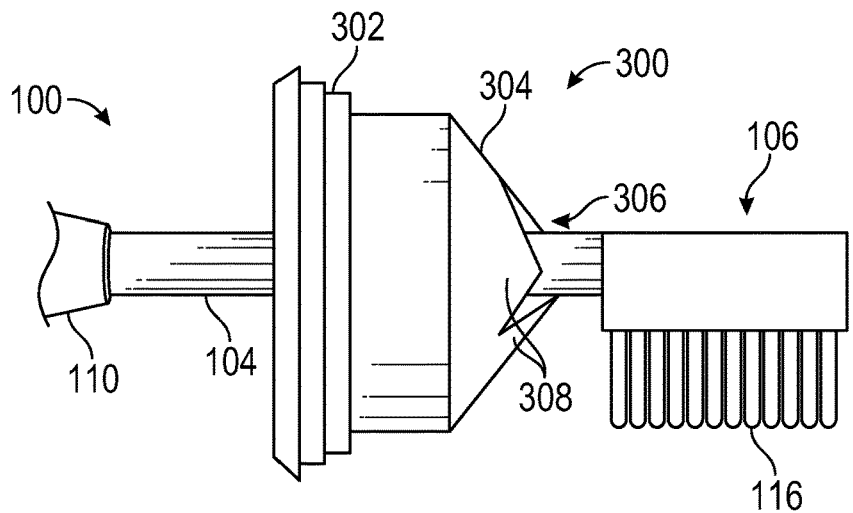

Referring now to FIGS. 5A-5C, side views of a septum 300 are shown, according to an exemplary embodiment. The septum 300 includes a base 302 and a crown portion 304 forming an opening 306. The crown portion 304 includes two or more flexible sections 308 separated by a slice in the septum material that defines the opening 306. As shown in FIG. 5A, in a natural state, the flexible sections meet together. The septum 300 as shown in FIG. 5A is thus in a closed configuration. However, the flexible sections 308 are configured to separate and thereby open the opening 306 when subject to a force. For example, FIG. 5B shows the toothbrush 100 entering through the opening 306 of the septum 300. FIG. 5C shows the head 106 of the toothbrush 100 having substantially passed through the opening 306 of the septum 300.

Accordingly, in some embodiments, the septum 300 is coupled to the internal chamber 206 of the oral fluid container 200 (e.g., at the inlet 208 or the outlet 210). The flexible sections 308 allow the toothbrush 100 to enter and exit through the opening 306 of the septum 300. However, because the septum 300 is naturally in a closed configuration, the septum 300 provides additional protection against spills, thereby increasing the spill-resistance of the oral fluid container 200, while maintaining an opening for the toothbrush 100. In some embodiments, the septum 300 also removes excess oral fluid 204 when the toothbrush 100 is removed from the internal chamber 206 by pulling the toothbrush 100 in the opposite direction through the septum 300 (e.g., because the two or more flexible sections 308 press excess oral fluid 204 from the toothbrush 100).

Figure 6C:
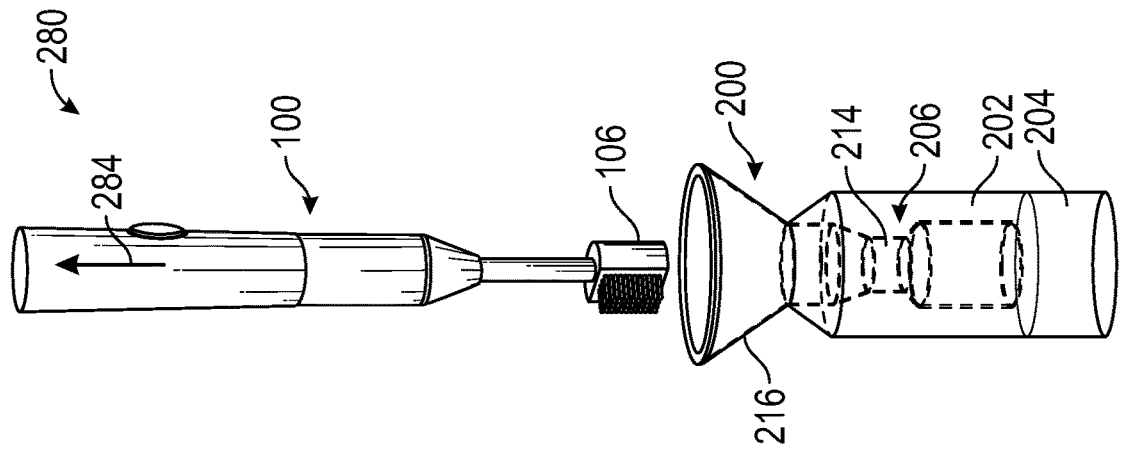
FIGS. 6A-6C depict steps of using an oral care system including the toothbrush of FIG. 1 and the unit dose oral fluid container of FIG. 2, according to an exemplary embodiment.
Figure 6B:
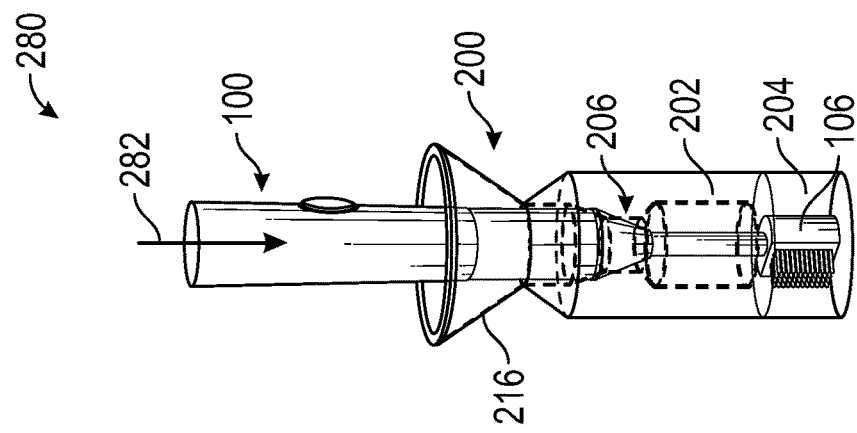
Figure 6A:
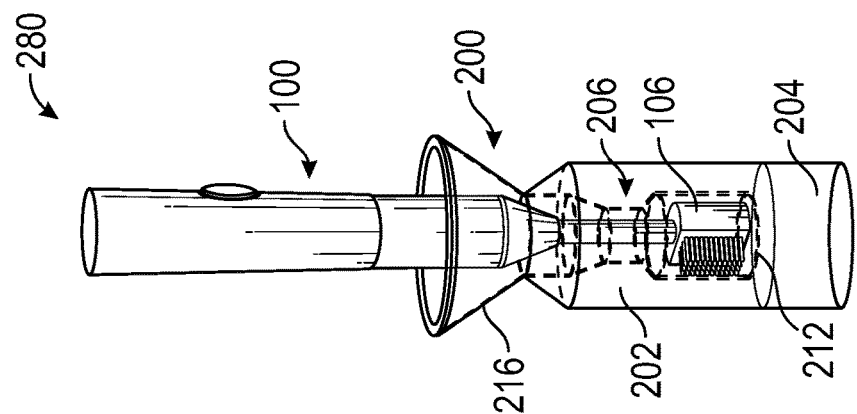

Referring now to FIGS. 6A-6C, a method of using an oral care system 280 including a toothbrush (e.g., toothbrush 100) and a unit dose oral fluid container (e.g., oral fluid container 200) is depicted according to an exemplary embodiment. FIG. 6A shows the oral care system 280 in a storage configuration with the toothbrush 100 held in the internal chamber 206 of the container 200. As such, the seal 212 is still intact, and the receptacle 202 is filled with oral fluid 204. While the embodiment shown in FIG. 6A includes a seal 21 to prevent the toothbrush 100 from entering the oral fluid container 200 too early, the oral care system 280 may alternatively use any other mechanism that prevents the toothbrush 100 from being removed from the internal chamber 206 and/or moved into the oral fluid 204 prior to use (e.g., such as the septum 300).

To begin using the oral care system 280, the patient or care provider pushes the toothbrush 100 in the direction depicted by arrow 282 in FIG. 6B to penetrate a penetrable barrier separating the toothbrush 100 from the oral fluid 204. In the embodiment shown, the penetrable barrier is the seal 212, though the oral fluid container 200 could additionally or alternatively include, for example, the septum 300. The toothbrush 100 then becomes exposed to the oral fluid 204 in the receptacle 202 and can be pushed through the outlet 210 into the oral fluid 204 to become saturated. As shown in FIG. 4C, the patient or care provider then pulls the toothbrush 100 in the direction depicted by arrow 284 in FIG. 6C out of the internal chamber 206 to initiate oral treatment. As the toothbrush 100 is pulled out of the internal chamber 206, the neck portion 214 squeezes the head 106 of the toothbrush 100 to remove excess oral fluid 204. Additionally, in embodiments including a septum 300, the flexible sections 308 of the crown portion 304 squeeze excess oral fluid 204 from the toothbrush 100. The patient or care provider may then use the toothbrush 100 in a standard fashion to brush the patent's teeth. During or after brushing, the patient spits into the funnel 216 to remove oral fluid from the patient's mouth. When the patient has finished the oral care treatment, the oral care system 280 is to be disposed. In some arrangements, the patient or care provider reinserts the toothbrush 100 into the internal chamber 206 before disposing of the oral care system 280.

Figure 7:
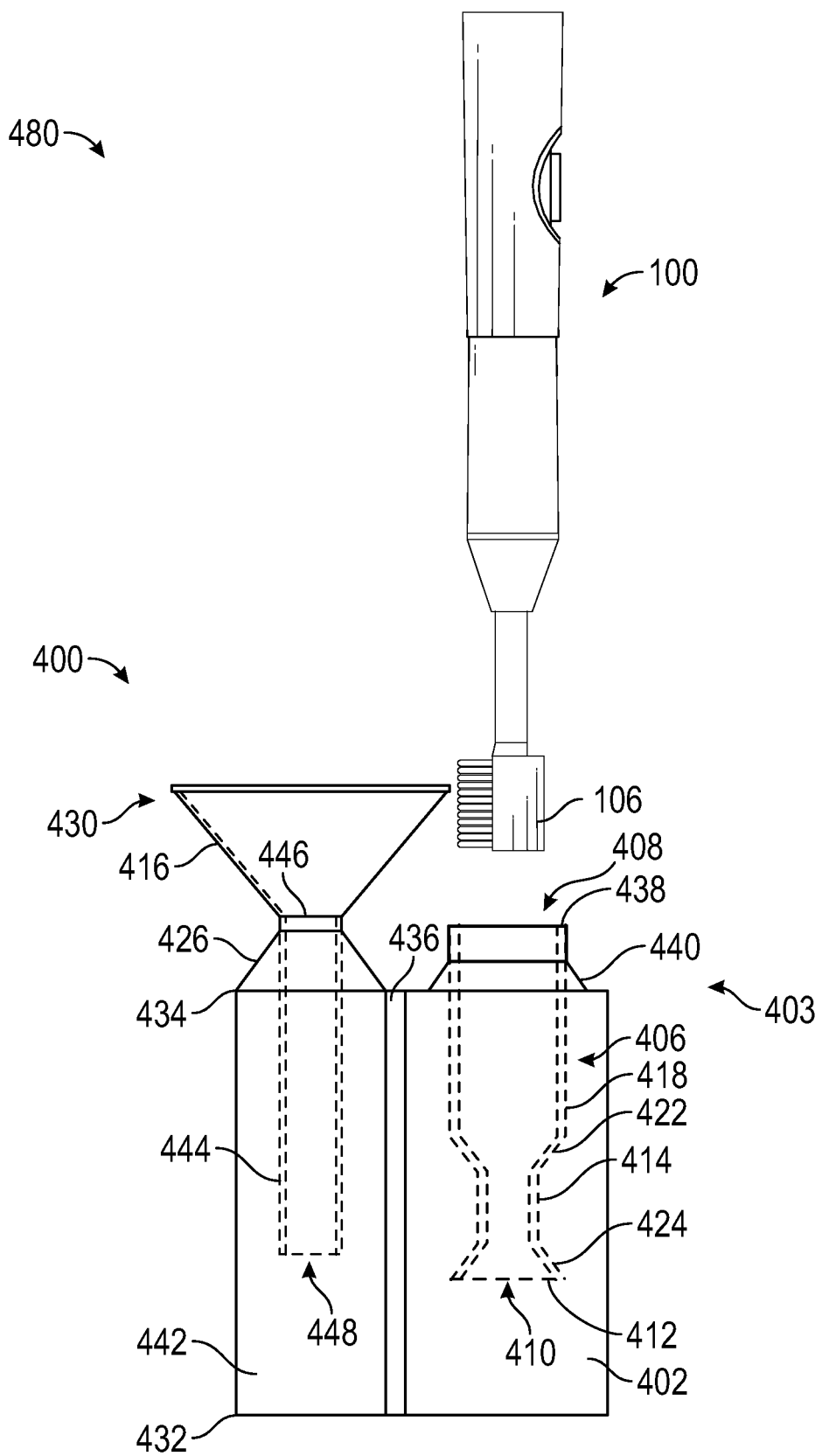
FIG. 7 is a schematic side view of an oral care system, according to another exemplary embodiment.

Referring now to FIG. 7, a schematic side view of an oral care system 480 is shown, according to another exemplary embodiment. The oral care system 480 again includes a toothbrush, shown as the toothbrush 100 and a unit dose oral fluid container, shown as oral fluid container 400. However, unlike the oral care system 280, the oral care system 480 includes a separate repository container 403 and waste container 430. As shown, the repository container 403 and the waste container 430 are connected via a bottom edge 432 and a top edge 434 and are separated by a gap 436 such that the repository container 403 and the waste container 430 do not interfere with one another. As shown in FIG. 7, the repository container 403 and the waste container 430 are entirely separate containers, though in other embodiments, the repository container 403 and the waste container 430 may be at least partially connected (e.g., at the bottom of the repository container 403 and the waste container 430).

As shown, the repository container 403 defines a receptacle 402 in the interior of the repository container 403 configured to hold an oral fluid, such as antiseptic. For example, in some embodiments, the receptacle 402 is configured to hold 9.5 mL of oral fluid. The receptacle 402 is coupled to a top portion 438 with an inlet 408 via a conical extension 440. The top portion 438 and the inlet 408 are sized to allow insertion and removal of the toothbrush 100.

The repository container 403 also includes an internal chamber 406. Similar to the internal chamber 206, the internal chamber 406 includes an outlet 410 providing a connection between the internal chamber 406 and the receptacle 402. The internal chamber 406 is defined by a first chamber 418 that is coupled to the top portion 438. A funnel portion 422 couples the first chamber 418 to a neck portion 414. The outlet 410 is defined by an inverted funnel portion 424, which is coupled to the neck portion 414 at the other end of the neck portion 414. In some embodiments, the outlet 410 is covered by a seal 412 prior to use. In other embodiments, a seal or other type of penetrable barrier is located in another portion of the internal chamber 406 and/or the internal chamber 406 includes a septum (e.g., similar to the septum 300). Similar to the internal chamber 206 of the oral fluid container 200, the internal chamber 406 provides housing for the toothbrush 100 while not in use. Additionally, the neck portion 414 (and/or, in some embodiments, a septum) is configured to remove excess oral fluid 204 from the toothbrush 100 as the toothbrush is being removed from the internal chamber 406 for use (e.g., by pressing the excess oral fluid 204 from the head 106 of the toothbrush 100 through a squeezing effect).

The waste container 430 includes a funnel 416 and a receptacle 442 that holds the brushing waste from a patient using the oral care system 480. The funnel 416 is coupled to the receptacle 442 via a conical expansion region 426. The funnel 416 provides a larger opening for a patient to spit brushing waste into when the patient is using the oral care system 480. The waste container 430 also includes an internal chamber 444, coupled to the funnel 416 at a base 446 of the funnel 416, that facilitates movement of the brushing waste from the funnel 416 to the receptacle 442. The internal chamber 444 includes an outlet 448 through which the brushing waste passes into the receptacle 442.

In some embodiments, the waste container 430 and the repository container 403 are also dimensioned to be spill-resistant, similar to the oral fluid container 200 described above. In some embodiments, the dimensions and/or dimension ratios of the oral care system 480 are the same as the dimensions and/or dimension ratios of similar components in the oral fluid container 200 (e.g., as shown in FIG. 3).

Figure 8:
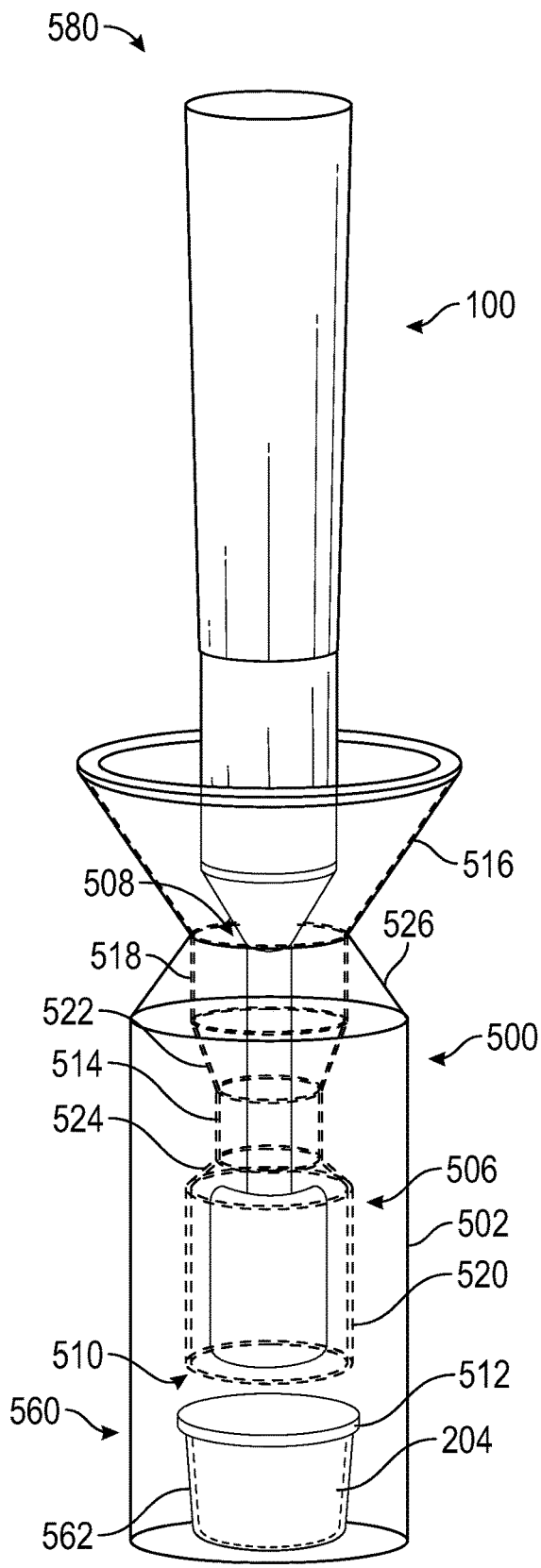
FIG. 8 is a schematic side view of an oral care system, according to another exemplary embodiment.

Referring now to FIG. 8, a schematic side view of an oral care system 580 is shown, according to another exemplary embodiment. The oral care system 580 includes the a toothbrush, shown as the toothbrush 100, and a unit dose oral fluid container, shown as oral fluid container 500. In various arrangements, the unit dose oral fluid container 500 of FIG. 8 is substantially similar to the unit dose oral fluid container 200 of FIG. 2. Accordingly, the oral fluid container 500 is shaped similarly to the oral fluid container 200 and includes a receptacle 502 and an internal chamber 506 in an interior portion of the oral fluid container 500 and a funnel 516 similar to the receptacle 202, internal chamber 206, and funnel 216 of the oral fluid container 200. The receptacle 502 is coupled to the funnel 516 via a conical expansion region 526. Further, similar to the internal chamber 206, the internal chamber 506 has an hourglass shape with an inlet 508 defined by a first chamber 518 that is coupled to the funnel 516, a second funnel portion 522 connecting the first chamber 518 to a neck portion 514, and an inverted funnel portion 524 connecting the neck portion 514 to a second chamber 520 that defines an outlet 510. As such, in various arrangements, the oral care system 580 is used similarly to the oral care system 280 described above.

However, unlike the oral fluid container 200, the unit dose oral fluid container 500 includes an oral fluid cup 560 configured to serve as a repository for the oral fluid 204. As such, in the oral fluid container 200, the oral fluid 204 is contained within the oral fluid cup 560 instead of residing in the receptacle 502. In some embodiments, the oral fluid cup 560 is coupled to the unit dose oral fluid container 500. For example, the oral fluid cup 560 is coupled to the container 500 by an attachment mechanism (e.g., glue) or an attachment device. Alternatively, the oral fluid cup 560 is constructed as a unitary piece with the container 500. In other embodiments, the oral fluid cup 560 is sized to securely fit within the unit dose oral fluid container 502, such as by a snap fit engagement.

The oral fluid cup 560 includes a base 562 that holds the oral fluid 204. In the embodiment shown in FIG. 8, the base 562 is cylindrical with a circular cross section. However, in other embodiments, the oral fluid cup 560 may have another cross-sectional shape, such as a circular cylinder or a square cylinder, or may have a varying diameter (e.g., be formed in a conical shape). A seal 512 extends across a top of the base 562. In various arrangements, the seal 512 is made of a plastic material, a foil material, or a similar material that can be punctured with a small force. The seal 512 may span the entire diameter of the receptacle 502, may span only the base 562, or may span any portion therebetween. In the embodiment of FIG. 8, the seal 512 of unit dose oral fluid container 500 replaces the seal 212 that spans the outlet 210 of the unit dose oral fluid container 200. As such, to use the oral care system 580, the patient must press the toothbrush 100 against the seal 512 with enough force that it breaks or is otherwise breached. In some cases, manufacturing a unit dose oral fluid container with an oral fluid cup having a seal (e.g., as described herein with respect to FIG. 7, FIG. 8, and FIGS. 10A and 10B) provides manufacturing advantages over the unit dose oral fluid container 200 with the seal 212. Alternatively, in other embodiments, the oral fluid cup 560 may include a different penetrable barrier, such as a cover with an internal cross cut.

Figure 9:
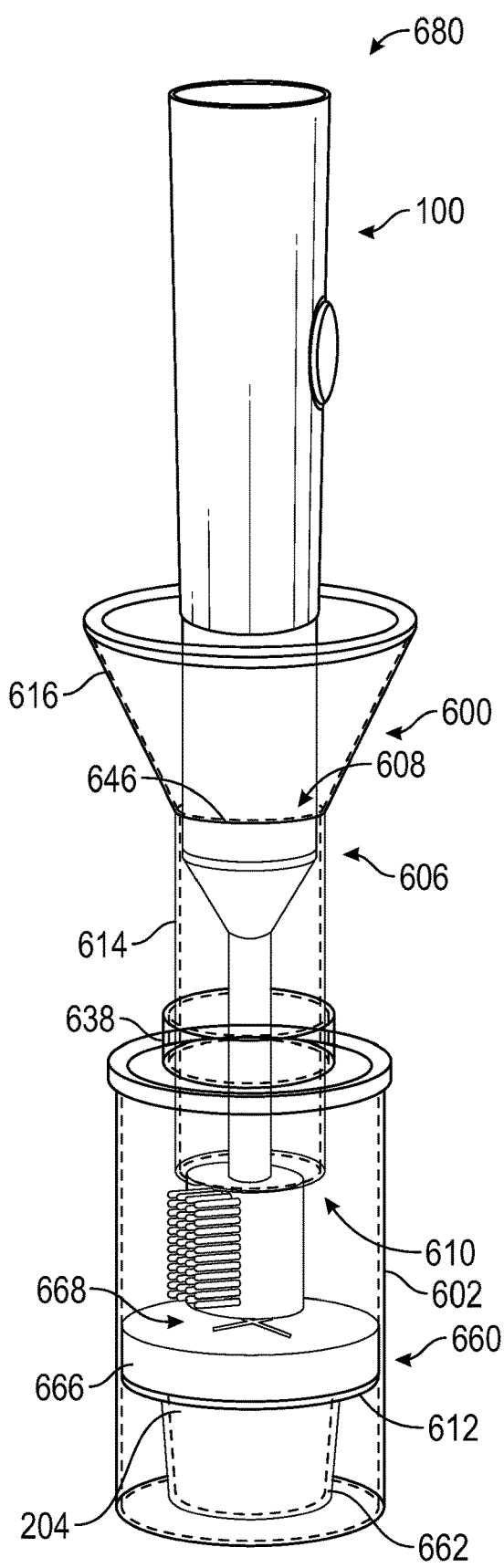
FIG. 9 is a schematic side view of an oral care system, according to another exemplary embodiment.

Referring now to FIG. 9, a schematic side view of an oral care system 680 is shown, according to another exemplary embodiment. The oral care system 680 includes a toothbrush, shown as toothbrush 100, and a unit dose oral fluid container, shown as oral fluid container 600. In various arrangements, the unit dose oral fluid container 600 is configured somewhat similar or substantially similar to the unit dose oral fluid container 200 shown in FIG. 2. As such, the oral fluid container 600 includes a receptacle 602 in an interior of the oral fluid container and a funnel 616. The oral fluid container 600 also includes a chamber 606, though the chamber 606 is configured differently from the internal chamber 206 of the oral fluid container 200. In particular, the chamber 606 of unit dose oral fluid container 600 differs from the previously described inner chambers in that it does not have a neck portion with a decreased diameter. Instead, the chamber 606 has a substantially cylindrical shape and a substantially uniform cross section extending between an inlet 608 and an outlet 610. The inlet 608 provides a connection between the funnel 616 and the chamber 606, and the outlet 610 provides a connection between the chamber 606 and the receptacle 602. The uniform cross section of the chamber 606, as well as the cross sections of the receptacle 602 and the funnel 616, are in any shape that facilitates the use of the oral care system 680, such as circular, elliptical, oblong, etc.

Further, as shown in FIG. 9, the chamber 606 has a portion that is internal to the receptacle 602 and a portion that extends above the receptacle 602. The portion of the chamber 606 that extends above the receptacle 602 is housed in a cylindrical neck portion 614. The cylindrical neck portion 614 is coupled to and sized according to a base 646 of the funnel 616, which also defines the inlet 608 of the chamber 606. Additionally, the cylindrical neck portion 614 is coupled to and sized according to a top portion 638 of the receptacle 602. In this way, the cylindrical neck portion 614 connects the funnel 616 to the receptacle 602, thereby allowing liquid to flow from the funnel 616 through the cylindrical neck portion 614 and into the receptacle 602. As such, the oral care system 680 may be used similarly to the oral care system 280 described above (e.g., by inserting the toothbrush 100, through the chamber 606, to be coated with oral fluid 204, removing the toothbrush from the receptacle 602 for use, and spitting into the receptacle 602 via the funnel 616).

In some embodiments, the funnel 616, the chamber 606, and the receptacle 602 are manufactured as a single piece. In other embodiments, the funnel 616, the chamber 606, and/or the receptacle 602 are manufactured as two or more pieces. For example, the funnel 616 and the chamber 606 are manufactured as a single piece that slidably fits into the top portion 638 of the receptacle 602. Additionally, in various arrangements, the receptacle 602 and the top portion 638 are manufactured as a single piece or as separate pieces. For example, the receptacle 602 is manufactured as an open-topped cylinder, and the top portion 638 is configured to snap into the open top of the receptacle 602.

Similar to unit dose oral fluid container 500, the unit dose oral fluid container 600 also includes an oral fluid cup 660 configured to serve as a repository for the oral fluid 204. As such, the oral fluid 204 is contained within the oral fluid cup 660 instead of residing in the receptacle 602. In various embodiments, the oral fluid cup 660 is coupled to the unit dose oral fluid container 600 as described above with respect to the oral fluid cup 560 and the unit dose oral fluid container 500. The oral fluid cup 660 includes a base 662 that holds the oral fluid 204. In the embodiment of FIG. 9, the base 662 is cylindrical with a circular cross section. However, in other embodiments, the base 662 may take on various cross-sectional shapes, such as a circular cylinder or a square cylinder, or may have a varying diameter (e.g., be formed in a conical shape). Further, in the embodiment of FIG. 9, the oral fluid cup 660 is sized to hold between 1 and 15 mL of oral fluid 204, such as oral fluid (e.g., sized to hold 7 mL of the oral fluid 204).

As shown in FIG. 9, a seal 612 also extends across a top of the base 662. In various arrangements, the seal 612 is made of a plastic material, a foil material, or a similar material that can be punctured with a small force. Similar to the seal 512, the seal 612 may span the entire diameter of the receptacle 602, may span only the top of the base 662, or may span any portion therebetween. In the embodiment of FIG. 9, the seal 612 of the unit dose oral fluid container 600 replaces the seal 212 that spans the outlet 210 of the unit dose oral fluid container 200. As such, to use the oral care system 680, the patient must press the toothbrush 100 against the seal 612 with enough force that it breaks or is breached.

As shown, the unit dose oral fluid cup 660 further includes a foam cover 666 positioned on top of the seal 612. The foam cover 666 has an internal cross cut 668 extending through the foam cover 666. In some embodiments, the foam cover 666 is a disk with a height of approximately 0.6 cm (0.25 inches). In other embodiments, the height of the foam cover 666 is in the range of approximately 0.25 to 2.5 cm (0.1 to 1.0 inches). The foam cover 666 is described herein as made of foam, but in other embodiments, the cover 666 is instead made of a different material (e.g., rubber, sponge, etc.). Without any force applied, the internal cross cut 668 of the foam cover 666 remains in a closed position. However, the internal cross cut 668 of the foam cover 666 is configured to separate and thereby open the foam cover 666 when subject to a substantially perpendicular force in either direction, for example, by a force provided by the toothbrush 100. Accordingly, the foam cover 666 is coupled to the receptacle 602 and/or the top of the oral fluid cup 660 and allows the toothbrush 100 to enter and exit the oral fluid cup 660 through the foam cover 666. In this way, the foam cover 666 serves as an additional penetrable barrier and provides additional protection against spills of the oral fluid 204 from the oral fluid cup 660, thereby increasing the spill-resistance of the oral fluid container 600, while maintaining an opening for the toothbrush 100.

In use, once the toothbrush 100 passes through the internal cross cut 668 of the foam cover 666, the toothbrush is pressed against the seal 612 to break or breach the seal 612, allowing the toothbrush 100 to access the oral fluid 204. The toothbrush 100 is then removed from the oral fluid cup 660 via the internal cross cut 668 of the foam cover 666 for use. In some embodiments, the foam cover 666 also removes excess oral fluid 204 from the toothbrush head when the toothbrush 100 is removed from the cup 660 through foam cover 666 (e.g., by pressing out and/or absorbing the excess oral fluid 204 as the toothbrush 100 is drawn through the internal cross cut 668). In some embodiments, the foam cover 666 further absorbs excess oral fluid 204 from the oral fluid cup 660, for example, oral fluid 204 that comes into contact with the foam cover 666 because of tipping or sloshing of oral fluid along the walls of the oral fluid cup 660.

Figure 11A:
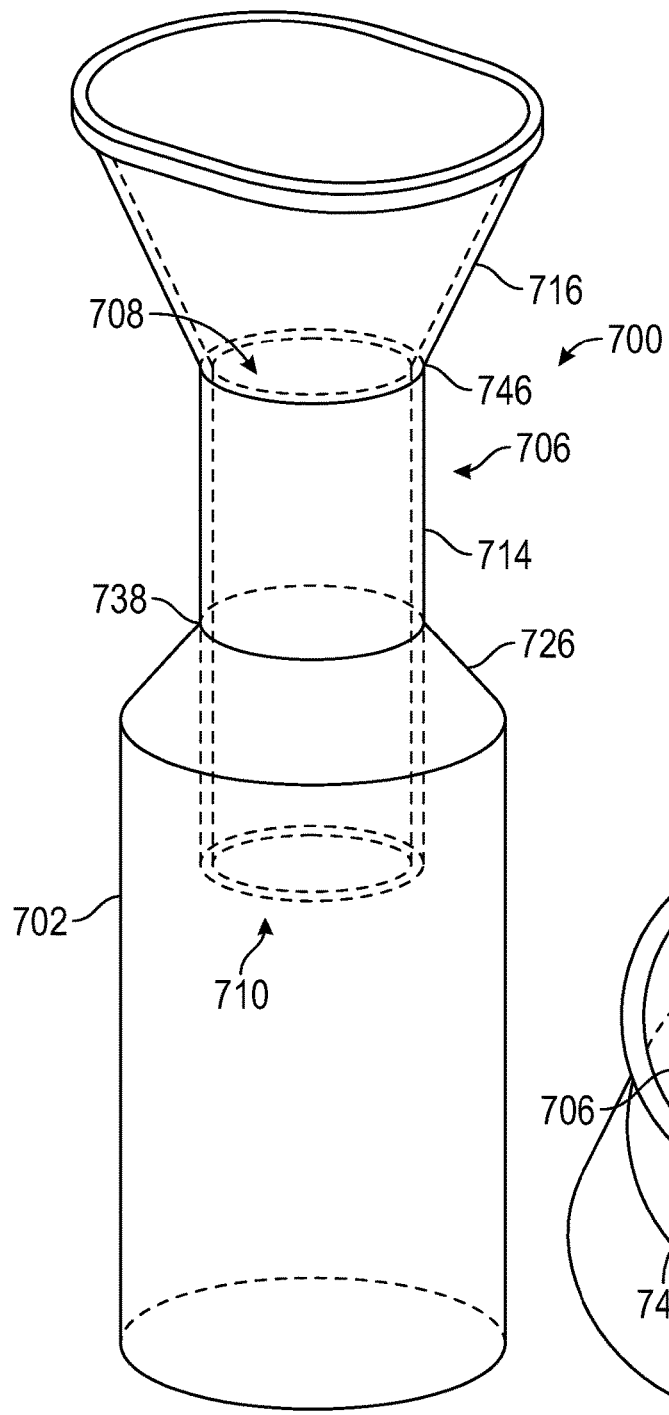
FIG. 11A is a schematic side view of the unit dose oral fluid container of the oral care system of FIGS. 10A and 10B, according to an exemplary embodiment.
Figure 11B:
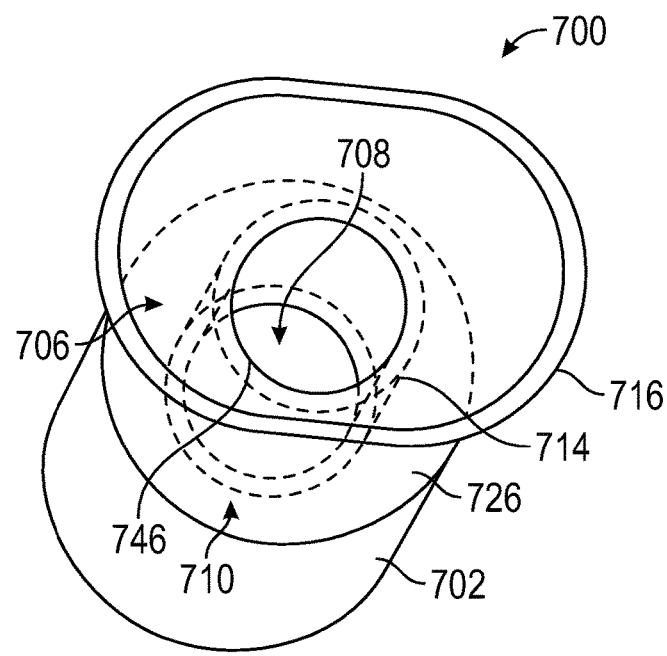
FIG. 11B is a schematic top view of the unit dose oral fluid container of FIG. 11A, according to an exemplary embodiment.

Referring now to FIGS. 10A and 10B, schematic side views of an oral care system 780 are shown, according to another exemplary embodiment. The oral care system 780 includes a toothbrush, shown as the toothbrush 100, and a unit dose oral fluid container, shown as oral fluid container 700. FIG. 11A depicts a schematic side view of the unit dose oral fluid container 700, and FIG. 11B depicts a schematic top view of the unit dose oral fluid container 700, according to an exemplary embodiment. As shown, in various arrangements, the unit dose oral fluid container 700 is configured similarly to the unit dose oral fluid container 600 of FIG. 9. Accordingly, the oral fluid container 700 includes a receptacle 702 defined by the interior of the oral fluid container 700, a funnel 716, and a chamber 706 that does not have a neck portion with a decreased diameter. Instead, similar to the chamber 606, the chamber 706 has a substantially cylindrical shape and a substantially uniform cross section extending between an inlet 708 and an outlet 710. The inlet 708 provides a connection between the funnel 716 and the chamber 706, and the outlet 710 provides a connection between the chamber 706 and the receptacle 702. The uniform cross sections of the chamber 706, as well as the cross sections of the funnel 716 and the receptacle 702, are in any shape that facilitates the use of the oral care system 780, such as circular, elliptical, oblong, etc.

Further, similar to the chamber 606 of the oral fluid container 600, the chamber 706 has a portion that is internal to the receptacle 702 and a portion that extends above the receptacle 702. The portion of the chamber 706 that extends above the receptacle 702 is housed in a cylindrical neck portion 714. The cylindrical neck portion 714 is coupled to and sized according to a base 746 of the funnel 716, which also defines the inlet 708 of the chamber 706. Additionally, the cylindrical neck portion 714 is coupled to and sized according to a top opening 738 defined in an expansion region of the receptacle 702. The expansion region 726 is conical in shape (e.g., shaped like an inverted funnel) and couples the portion of the receptacle 702 with a substantially constant diameter to the chamber 706. In this way, the cylindrical neck portion 714 connects the funnel 716 to the receptacle 702, thereby allowing liquid to flow from the funnel 716 through the cylindrical neck portion 714 and into the receptacle 702. Thus, referring back to FIGS. 10A and 10B, the oral care system 780 is used similarly to the oral care system 280 described above (e.g., by inserting the toothbrush 100 through the chamber 706 to be coated with oral fluid 204, removing the toothbrush from the receptacle 702 for use, and spitting into the receptacle 702 via the funnel 716). Additionally, as with the unit dose oral fluid container 600, the oral fluid container 700 is manufactured as a single piece or in multiple pieces.

Referring back to FIGS. 10A and 10B, similar to the unit dose oral fluid containers 500 and 600, the unit dose oral fluid container 700 also includes an oral fluid cup 760 configured to serve as a repository for the oral fluid 204. As such, the oral fluid 204 is contained within the oral fluid cup 760 instead of residing in the receptacle 702. In various arrangements, the oral fluid cup 760 is coupled to the unit dose oral fluid container 700 as described above with respect to the oral fluid cup 560 and the unit dose oral fluid container 500. The oral fluid cup 760 includes a base 762 that holds the oral fluid 204. In the embodiment of FIGS. 10A and 10B, the base 762 is cylindrical with a circular cross section. However, in other embodiments, the base 762 may take on various cross-sectional shapes, such as a circular cylinder or a square cylinder, or may have a varying diameter (e.g., be formed in a conical shape). Further, in various arrangements, the oral fluid cup 760 is sized to hold between 1 and 15 mL of the oral fluid 204, such as oral fluid (e.g., sized to hold 7-7.5 mL of the oral fluid 204).

As shown in FIGS. 10A and 10B, a seal 712 also extends across a top of the base 762, and, in various embodiments, the seal 712 is similar to the seals 512 and/or 612 described above. The unit dose oral fluid container 700 further includes a sponge cover 766 having an internal cross cut 768 through the foam cover. In various embodiments, the sponge cover 766 is configured and functions similarly to the foam cover 666 described above with respect to the unit dose oral fluid cup 660, except that the sponge cover 766 is made of a sponge material rather than a foam material. In other arrangements, however, the sponge cover 766 is made of a non-sponge material (e.g., rubber, foam, etc.).

Figure 12:
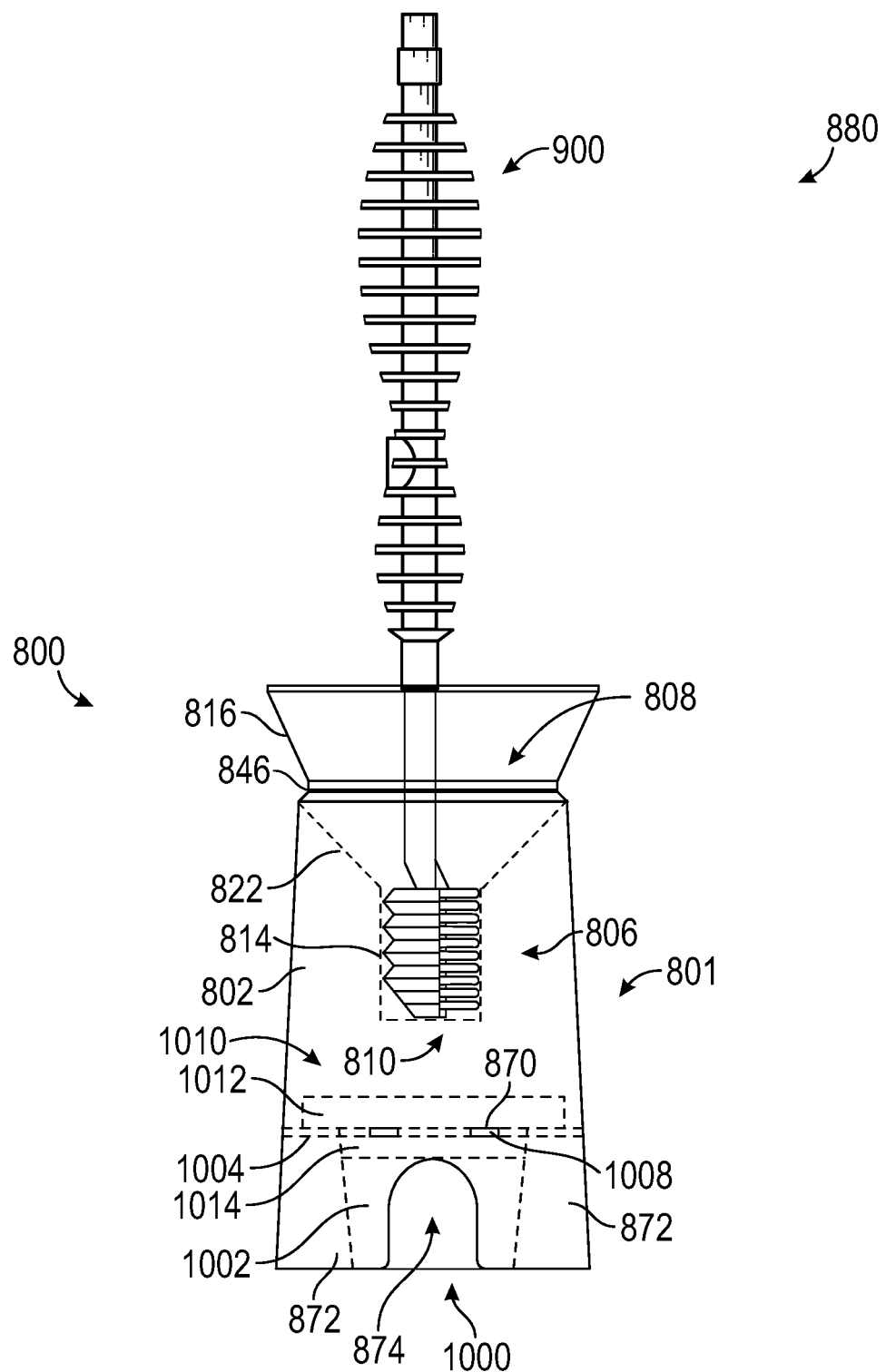
FIG. 12 is a schematic side view of an oral care system, according to another exemplary embodiment.
Figure 13:
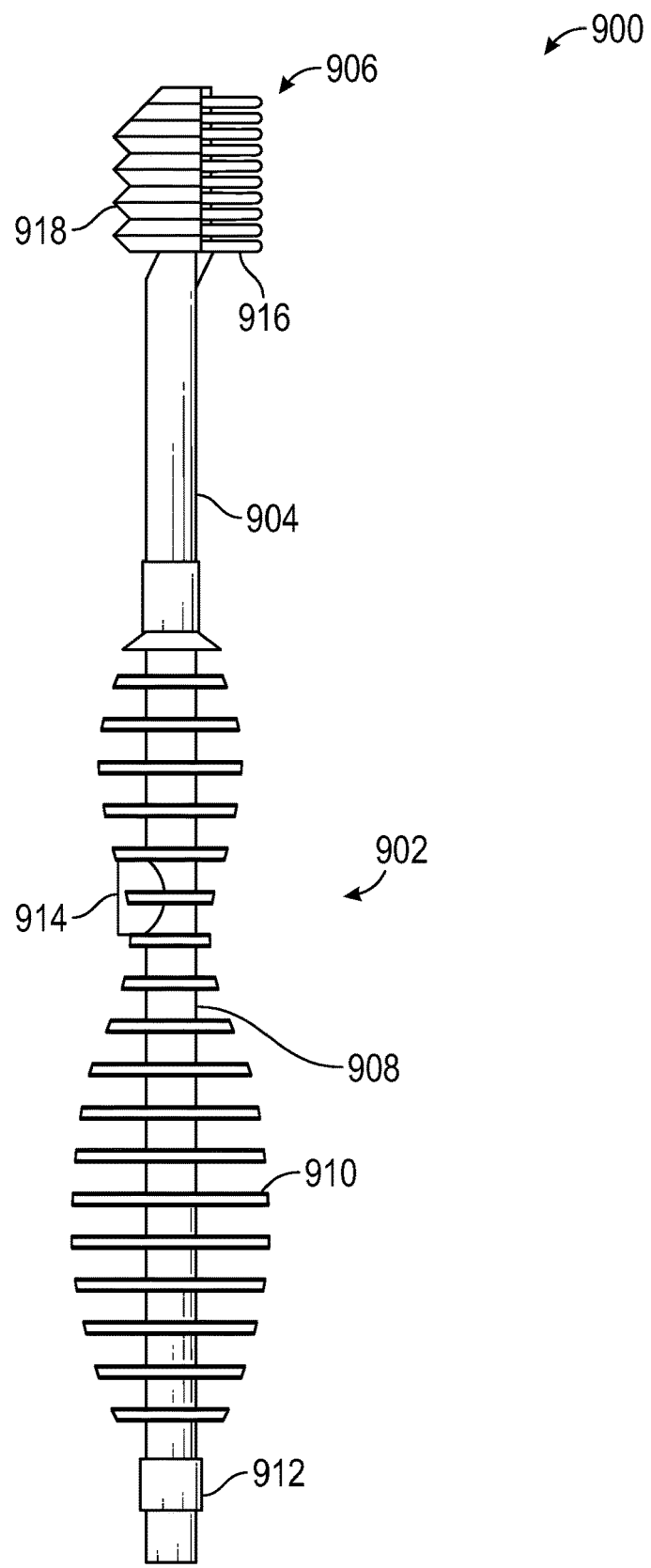
FIG. 13 is a side view of a toothbrush, according to another exemplary embodiment.

Referring now to FIG. 12, a schematic side view of an oral care system 880 is shown, according to another exemplary embodiment. The oral care system 880 includes a unit dose oral fluid container, shown as oral fluid container 800, and a toothbrush, shown as toothbrush 900. Referring to FIG. 13, a side view of the toothbrush 900 is shown, according to an exemplary embodiment. The toothbrush 900 includes a handle 902 coupled to a lower stem 904, which in turn is coupled to a head 906. The handle 902 includes an upper stem 908 with disc-like projections 910 extending from the upper stem 908. The diameters of the projections 910 vary along the length of the upper stem 908 to provide an ergonomically beneficial design. For example, the projections 910 provide a wider handle for the toothbrush so that patients with less gripping force or ability have an easier time gripping the toothbrush. As shown in FIG. 13, in some embodiments, the projections 910 are wider near the bottom of the toothbrush 900 and narrower near the location where the lower stem 904 and upper stem 908 meet. As further shown in FIG. 13, in certain embodiments, the projections 910 are also narrower near the center of the upper stem 908.

In various arrangements, the upper stem 908 is hollow to provide suction therethrough. Accordingly, as shown in FIG. 13, the upper stem 908 includes a suction port 912 configured to couple to a suction mechanism. Further, the upper stem 908 includes a projecting suction opening 914. The projecting suction opening 914 is positioned so that the patient can place a finger over the opening to activate suction through the upper stem 908. The lower stem 904, which extends between the upper stem 908 and the head 906, is hollow to allow suction to travel between the head 906 and the suction port 912.

The head 906 includes bristles 916 and a foam section 918. In some embodiments, the foam section 918 is located on both the back and sides of the head 906. In other embodiments, the foam section 918 is located on only one of the back or sides. Further, in some embodiments, the foam section 918 is glued to the head 906 of the toothbrush 900, while in other embodiments the foam section 918 is attached to the head 906 through another mechanism (e.g., through an interference fit). As shown in FIG. 13, in some embodiments, the foam section 918 has ridges to aid in cleansing. In various arrangements, the head 906 also includes at least one suction hole to provide for suction of fluids (e.g., saliva, antiseptic or other oral care fluid, etc.) from the mouth of the user. The at least one suction hole is located on a top, front, and/or back of the head 906.

In various arrangements, the toothbrush 900 is manufactured using cored out injection molding. In some embodiments, the toothbrush 900 is a unitary, single injection-molded piece forming the upper stem 908, projections 910, lower stem 904, and the head 906. In other embodiments, the toothbrush 900 is manufactured in separate pieces and assembled to form the completed toothbrush 900. For example, the upper stem 908 and the lower stem 904 are formed together as a single injection-molded piece or formed as separate pieces that are later connected together.

The toothbrush 900 is described herein with reference to the oral care system 880. However, it should be understood that the toothbrush 900 may be used with any of the oral care systems described herein. Moreover, it should further be understood that the oral care system 880 may be used with a differently designed toothbrush, such as the toothbrush 100.

Figures 14A, 14B:
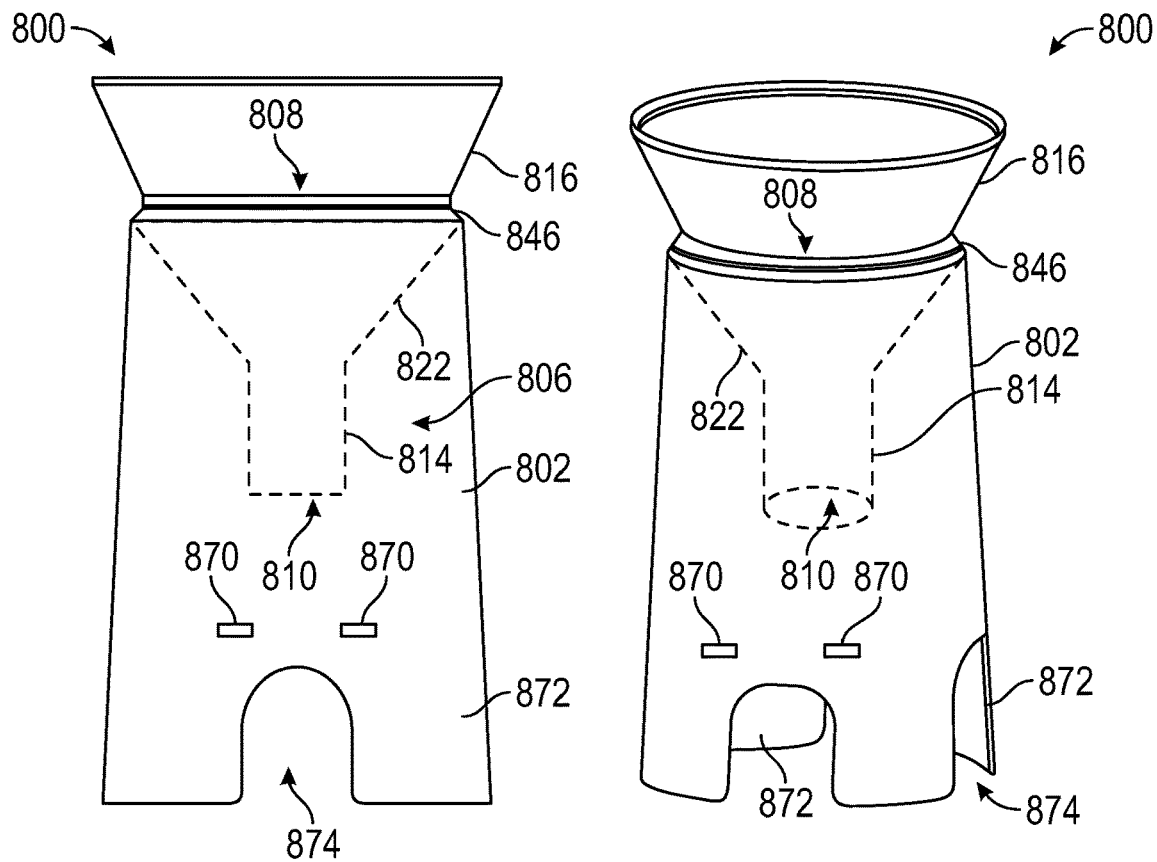
FIGS. 14A and 14B are schematic side views of an oral fluid bottle of FIG. 12, according to an exemplary embodiment.

With respect to the oral care system 880, as shown in FIG. 12, the unit dose oral fluid container 800 includes an oral fluid bottle 801 and a cylinder solution cup 200. Referring now to FIGS. 14A and 14B, schematic side views of the oral fluid bottle 801 are shown, according to an exemplary embodiment. The oral fluid bottle 801 includes a receptacle 802, a funnel 816 provided on a top portion of the receptacle 802, and an internal chamber 806 providing a channel between an interior of the receptacle 802 and the funnel 816. As shown, the receptacle 802 and the internal chamber 806 are both contained within an interior portion of the oral fluid bottle 801. The receptacle 802 is sized and configured to provide a stable base for the oral fluid bottle 801. In the embodiment shown, the receptacle 802 of the oral fluid bottle 801 is cylindrical, though in other embodiments the receptacle 802 has another shape (e.g., a rectangular shape).

The funnel 816 is coupled to the receptacle 802 at a base 846 of the funnel 816. The funnel 816 facilitates the passage of brushing waste to an internal portion of the receptacle 802 during or after the use of a toothbrush (e.g., toothbrush 900) by the patient. The funnel 816 provides a larger area for a patient to deposit the brushing waste into while brushing to minimize any mess associated with spitting into the oral fluid bottle 801. As shown in FIGS. 14A and 14B, in some embodiments, the funnel 816 lies above the main body of the receptacle 802 and extends into the receptacle 802 to form the internal chamber 806. The internal chamber 806 accordingly includes a second funnel portion 822 that narrows to a neck portion 814. Liquid can be received into the internal chamber 806 through an inlet 808 at the top of the second funnel portion 822 and flow out of the internal chamber 806 via an outlet 810 at the bottom of the neck portion 814. In certain embodiments, the receptacle 802, funnel 816, and internal chamber 806 are also a unitary body formed integral with one another. The oral fluid container 800 is configured to be used similarly to the oral fluid container 200 described above (e.g., by inserting the toothbrush 900 through the internal chamber 806 to be coated with oral fluid 204, removing the toothbrush from the receptacle 802 for use, and spitting into the receptacle 802 via the funnel 816). Accordingly, in various arrangements, the internal chamber 806 is sized to hold a toothbrush head (e.g., the toothbrush head 906), and the neck portion 814 is sized to press out excess oral fluid 204 from the toothbrush head 906 when the toothbrush 900 is removed from the oral fluid bottle 801 by pulling the toothbrush 900 through the internal chamber 806.

Additionally, the receptacle 802 is configured to receive a cylinder solution cup through a lower portion of the receptacle 802. As shown in FIGS. 14A and 14B, the receptacle 802 has an open bottom for receiving the cylinder solution cup, though in other embodiments, the receptacle 802 is structured to receive the cylinder solution cup differently (e.g., include a slot for sliding in the cylinder solution cup). In various embodiments, the receptacle 802 also includes legs 872 defining the area that receives the cylinder solution cup. The legs 872 are spaced apart to create openings 874 for the ease of inserting the cylinder solution cup into the receptacle 802. The receptacle 802 further includes apertures 870 for locking the cylinder solution cup into the receptacle 802. The apertures 870 may have various arrangements on the receptacle 802. For example, in some embodiments and as shown in FIGS. 14A and 14B, the receptacle 802 includes two sets of two apertures 870, opposite one another, near the bottom portion of the receptacle 802.

Figure 15:
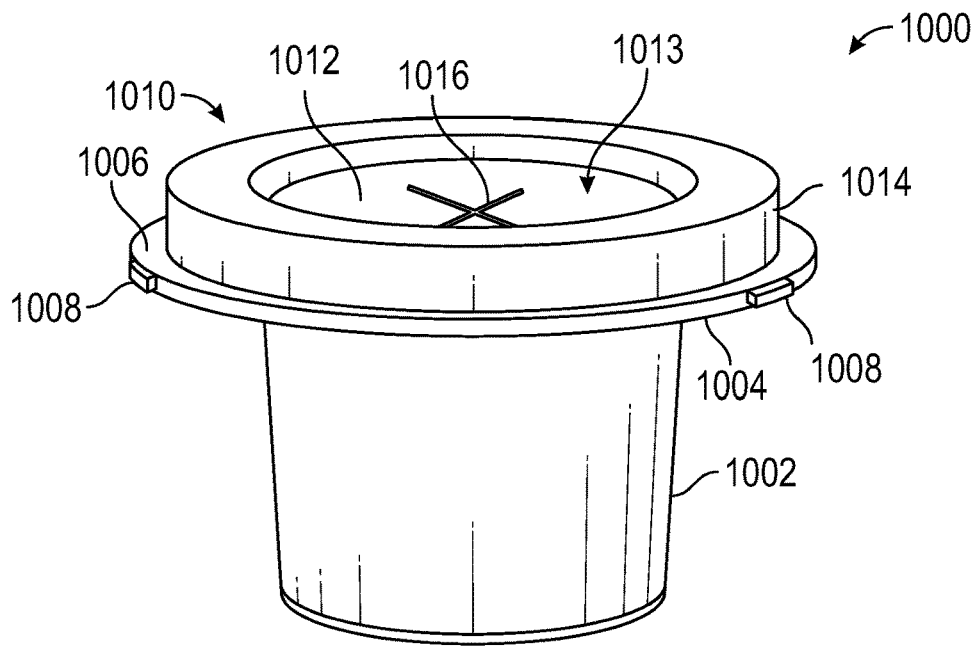
FIG. 15 is a side perspective view of a cylinder solution cup configured to fit into the oral fluid bottle FIGS. 14A and 14B, according to an exemplary embodiment.

Referring now to FIG. 15, a side perspective view of a cylinder solution cup 1000 is shown, according to an exemplary embodiment. The cylinder solution cup 1000 includes a cup base 1002 configured to serve as a repository for the oral fluid and receives brushing waste from a patient brushing his or her teeth. The cylinder solution cup 1000 is configured to hold a sufficient amount of oral fluid such that when the toothbrush 900 is dipped into oral fluid, the volume change in oral fluid due to displacement allows the head 906 of the toothbrush 900 to be substantially submerged in oral fluid while at the same time not spilling any of oral fluid out the top of the cup 1000. In some embodiments, the cylinder solution cup 1000 is configured to hold approximately 7.5 mL of oral fluid.

The cylinder solution cup 1000 includes a rim 1004 that defines a ledge 1006 and carries cup projections 1008. The cup projections 1008 are spaced to align with the apertures 870 of the oral fluid bottle 801 such that the cup projections 1008 can snap into the apertures 870 to lock the cylinder solution cup 1000 into the receptacle 802 of the oral fluid bottle 801. The cylinder solution cup 1000 also includes a upper portion 1010 that is wider than the cup base 1002. The upper portion 1010 includes a gasket or o-ring 1014 that rests on the ledge 1006 to provide a seal between the cylinder solution cup 1000 and the receptacle 802 once the cylinder solution cup 1000 is snapped into the oral fluid bottle 801.

Figure 16:
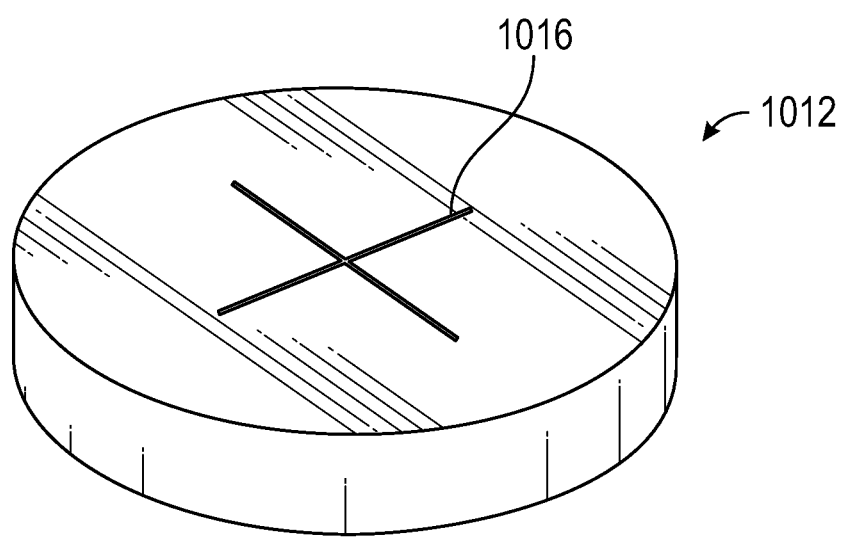
FIG. 16 is a side perspective view of a cover for the cylinder solution cup of FIG. 15, according to an exemplary embodiment.

The upper portion 1010 defines an opening 1013 at a top of the cylinder solution cup 1000. The opening 1013 holds a cover 1012, which is illustrated with greater detail in FIG. 16. The cover 1012 may be constructed of foam, rubber, or a similar flexible material and includes an internal cross cut 1016. Similar to the internal cross cut 668 of the cover 666, the internal cross cut 1016 allows the toothbrush 900 to enter and exit the cover 1012 and removes excess oral fluid from the toothbrush head 906. The cover 1012 is glued or otherwise affixed to, or rested upon, the cylinder solution cup 1000. In various embodiments, under the cover 1012, the cylinder solution cup 1000 includes a foil seal (not shown) to prevent oral fluid from escaping the cylinder solution cup 1000 before use. The level of oral fluid contained in the cup base 1002 is accordingly selected to allow for ease of sealing the cylinder solution cup 1000 without spilling oral fluid. The seal is broken by pushing the head 906 of the toothbrush 900 through the internal cross cut 1016 of the cover 1012 and through the seal, if provided, after which the head 906 of the toothbrush 900 can be at least partially submerged in the oral fluid contained in the cup base 1002. Accordingly, the seal and the cover 1012 serve as penetrable barriers that the toothbrush 900 must pass through in order to access the oral fluid.

Referring back to FIG. 12, the assembled oral care system 880 is shown. Accordingly, as can be seen through the opening 874 between the legs 872, the cylinder solution cup 1000 has been inserted into the oral fluid bottle 801 through the open bottom of the oral fluid bottle 801. The cylinder solution cup 1000 has also been snapped into the unit dose oral fluid container 800 via the apertures 870 and the cup projections 1008. The head 906 of the toothbrush 900 sits in the neck portion 814 of the internal chamber 806. The neck portion 814 of the internal chamber 806 is sized to hold the head 906 of the toothbrush 900 firmly in place, but the user may use a small force to move the head 906 of the toothbrush 900 within the internal chamber 806 for use. For example, to use the oral care system 880, the patient presses the head 906 of the toothbrush 900 through the outlet 810 of the internal chamber 806 into the receptacle 802. The patient further presses the toothbrush 900 into the cylinder solution cup 1000 by providing a sufficient force to press through the cover 1012 and the seal, if provided, of the cylinder solution cup 1000. The head 906 of the toothbrush 900 is then substantially covered by oral fluid contained within the cup base 1002 of the cup 1000 and removed from the receptacle 802 via the inlet 808 of the internal chamber 806. As shown in FIG. 12, the rim 1004 fits snugly against the walls of the receptacle 802. Accordingly, the patient can spit into the receptacle 802 via the funnel 816, and the tight fit between the cylinder solution cup 1000 and the receptacle 802 contains the brushing waste therein.

In some embodiments, the oral fluid bottle 801 and the cylinder solution cup 1000 are sized and shaped to provide a spill-resistant design, similar to the unit dose oral fluid container 200 described above. In particular, in various arrangements, the receptacle 802, funnel 816, and internal chamber 806 are sized and configured, based upon the volume of the oral fluid in the solution cup and/or expected volume of brushing waste to be received, such that even with tipping of the receptacle 802 onto its side, no fluid or little fluid flows into the internal chamber 806 via the outlet 810 to be spilled outside of the oral fluid bottle 801.

Figure 17:
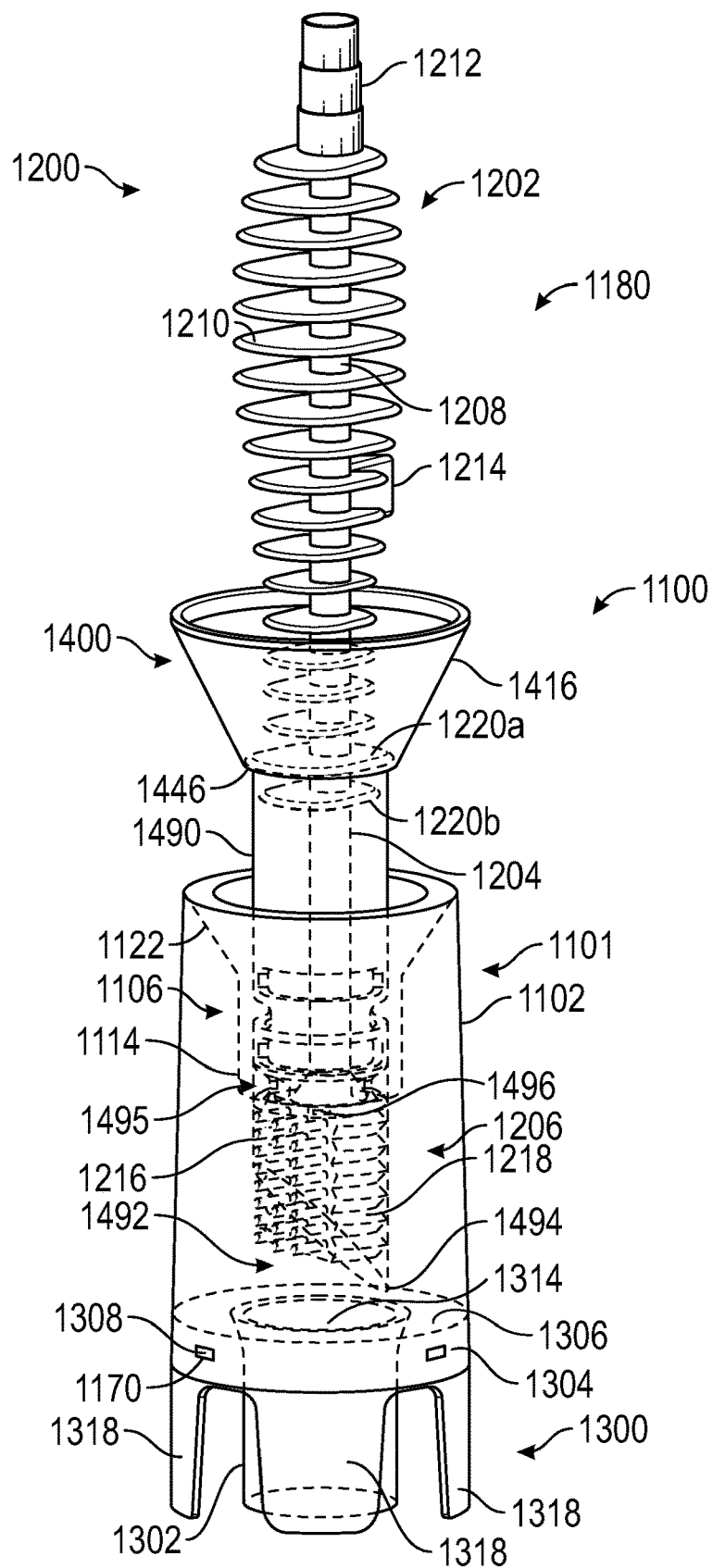
FIG. 17 is a schematic side view of an oral care system, according to another exemplary embodiment.
Figure 18A:
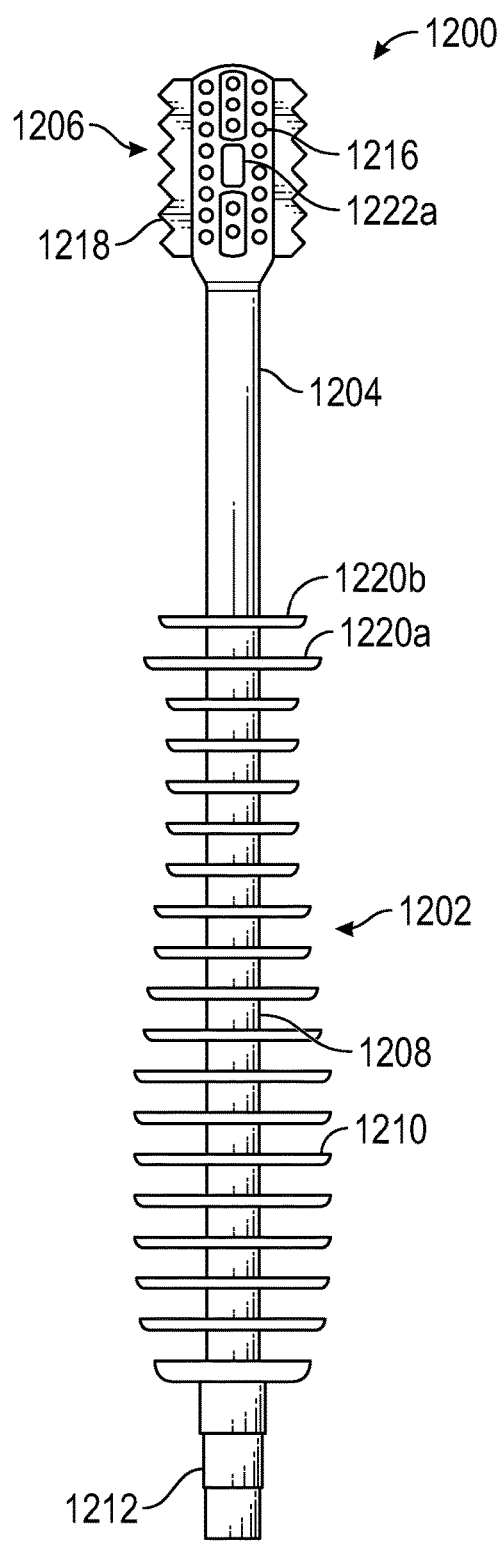
FIGS. 18A-18C are side views of a toothbrush, according to another exemplary embodiment.
Figure 18B:
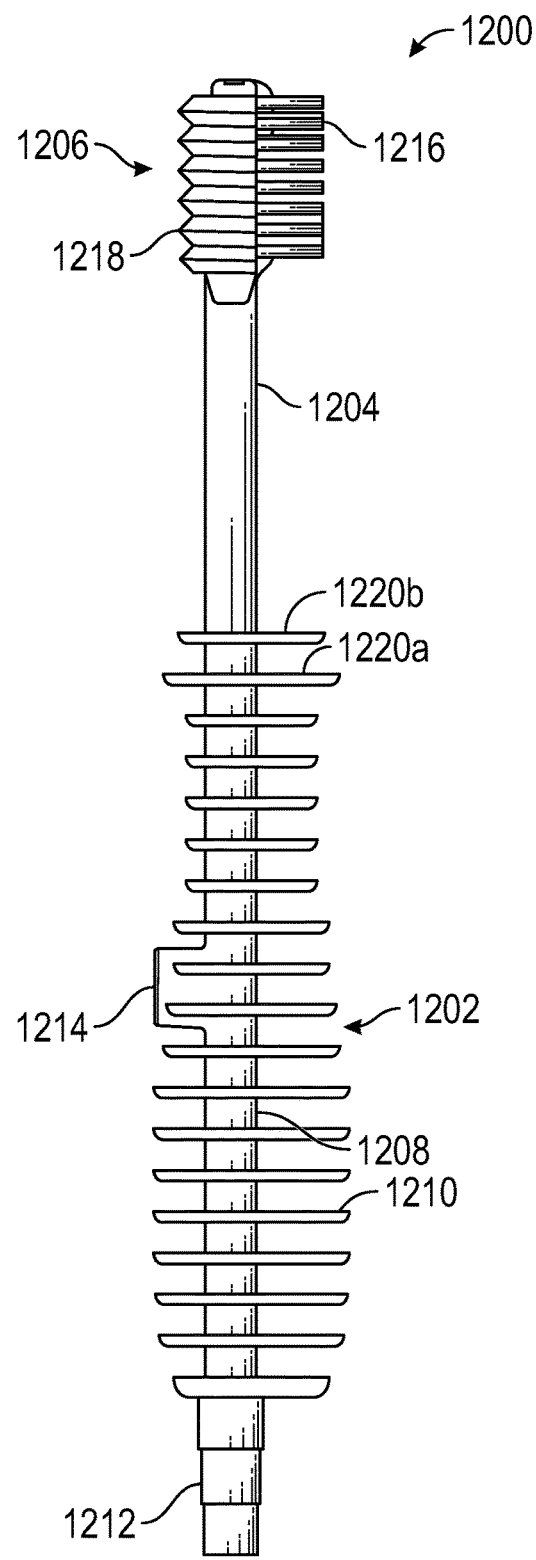
Figure 18C:
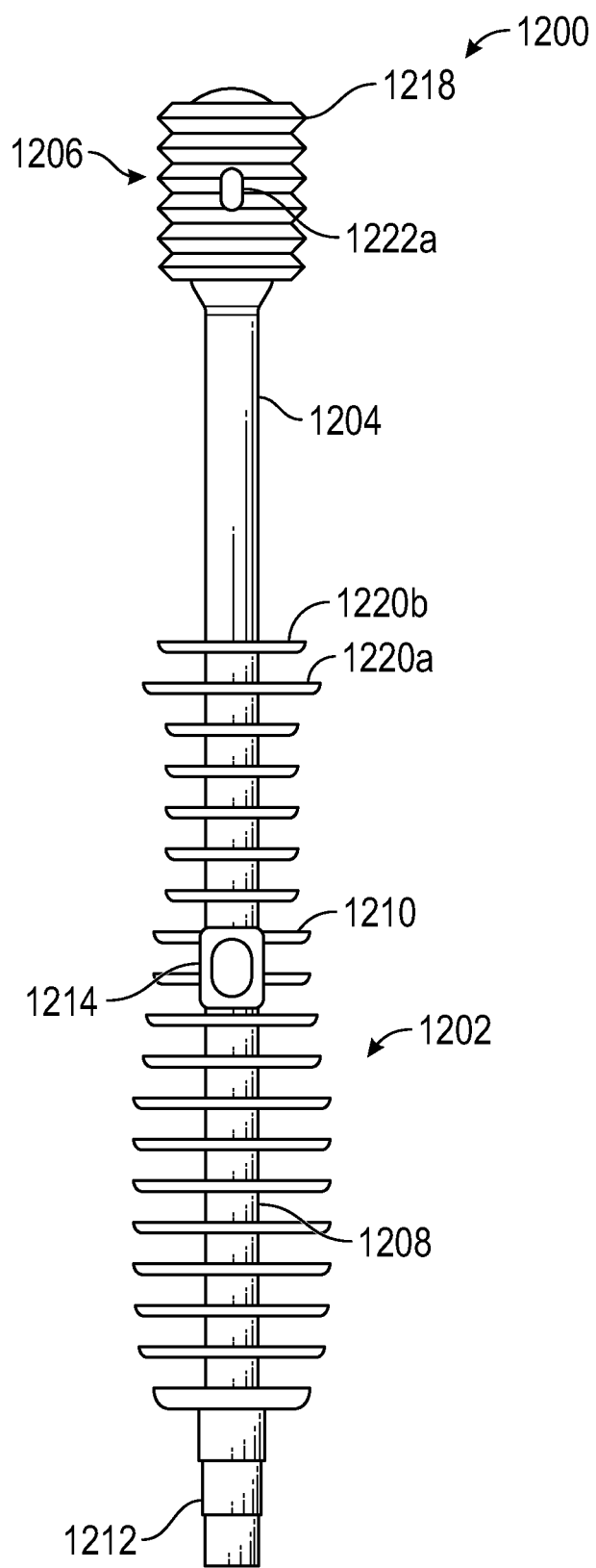

Referring now to FIG. 17, a schematic perspective side view of an oral care system 1180 is shown, according to another exemplary embodiment. The oral care system 1180 includes a unit dose oral fluid container, shown as oral fluid container 1100, and a toothbrush, shown as toothbrush 1200. Additionally, as shown, the unit dose oral fluid container 1100 includes an oral fluid bottle 1101, a cylinder solution cup 1300, and a spittoon straw 1400. Referring to FIGS. 18A-18C, side views of the toothbrush 1200 are shown, according to an exemplary embodiment. As shown, the toothbrush 1200 is configured similarly to toothbrush 900 shown in FIG. 13. The toothbrush 1200 includes a handle 1202 coupled to a lower stem 1204, which in turn is coupled to a head 1206. The head 1206 includes bristles 1216 and a foam section 1218. The handle 1202 includes an upper stem 1208 with disc-like projections 1210 extending from the upper stem 1208.

Like the projections 910, the diameters of the projections 1210 vary along the length of the upper stem 1208 to provide an ergonomically beneficial design. However, unlike the projections 910, the centers of the projections 1210 are offset from the upper stem 1208 such that the projections 1210 extend past the upper stem 1208 of the handle 1202 more in the direction of the bristles 1216 than in the direction of the foam section 1218 of the head 1206, as shown in FIG. 18B. Because the projections 1210 are offset from the upper stem, the toothbrush 1200 can be inserted into the spittoon straw 1400 as shown in FIG. 17 without crushing the bristles 1216. Additionally, the projections 1210 include a projection seal 1220a and a projection seal 1220b. The projection seals 1220a and 1220b are configured to block a center conduit of the spittoon straw 1400 to prevent contaminants (e.g., dust) from entering the interior of the oral fluid container 1100, as described in further detail below.

Figure 18D:
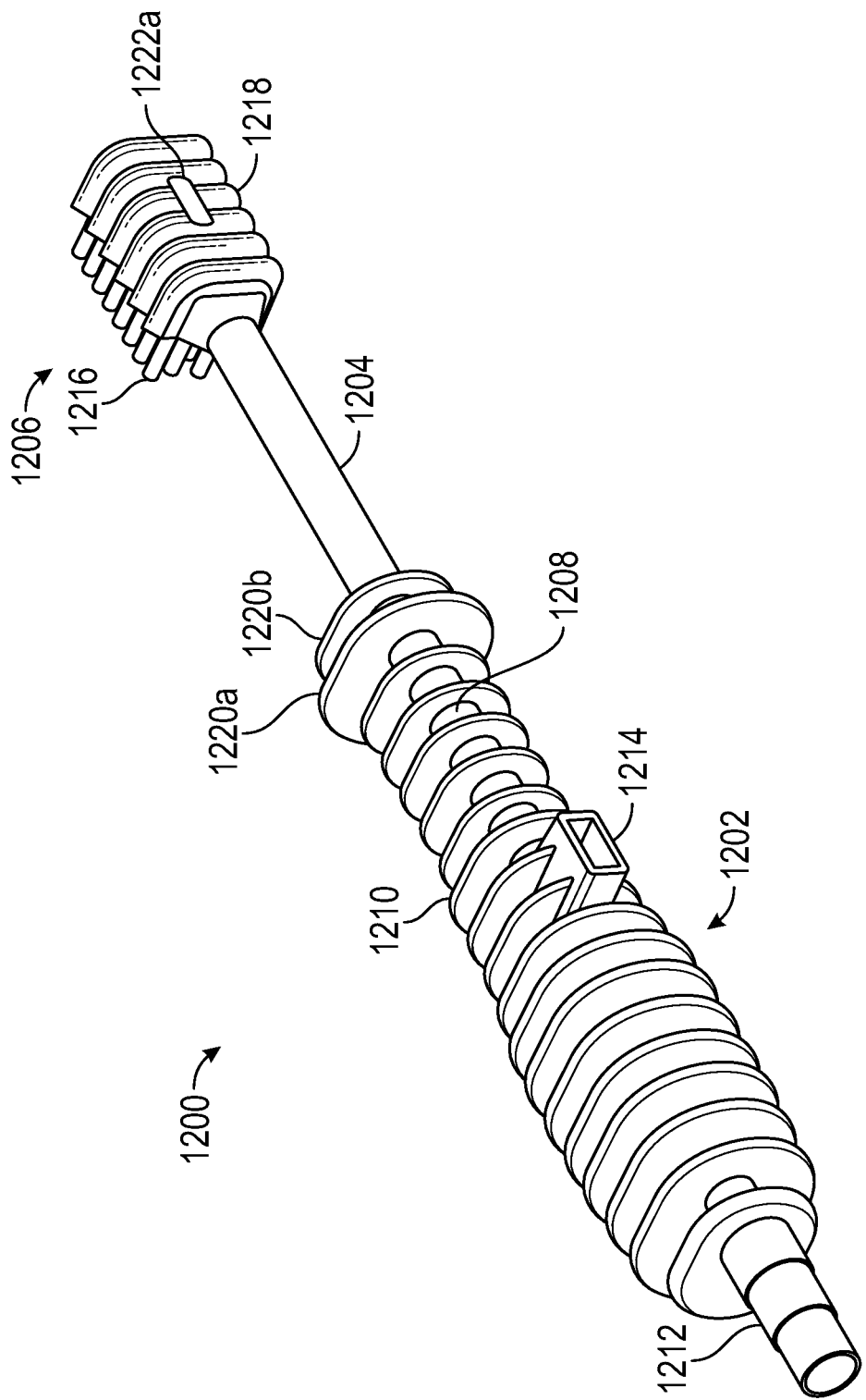
FIG. 18D is a side perspective view of the toothbrush of FIGS. 18A-18C, according to an exemplary embodiment.

In various arrangements, the upper stem 1208 is hollow to provide suction therethrough. Accordingly, the upper stem 1208 includes a suction port 1212 configured to couple to a suction mechanism, as shown in more detail in FIG. 18D illustrating a side perspective view of the toothbrush 1200. Further, the upper stem 1208 includes a projecting suction opening 1214. The projecting suction opening 1214 is positioned and extends beyond the projections 1220 so that the patient can place a finger over the opening to activate suction through the upper stem 1208. The lower stem 1204, which extends between the upper stem 1208 and the head 1206, is hollow to allow suction to travel between the head 1206 and the suction port 1212.

Figure 18E:
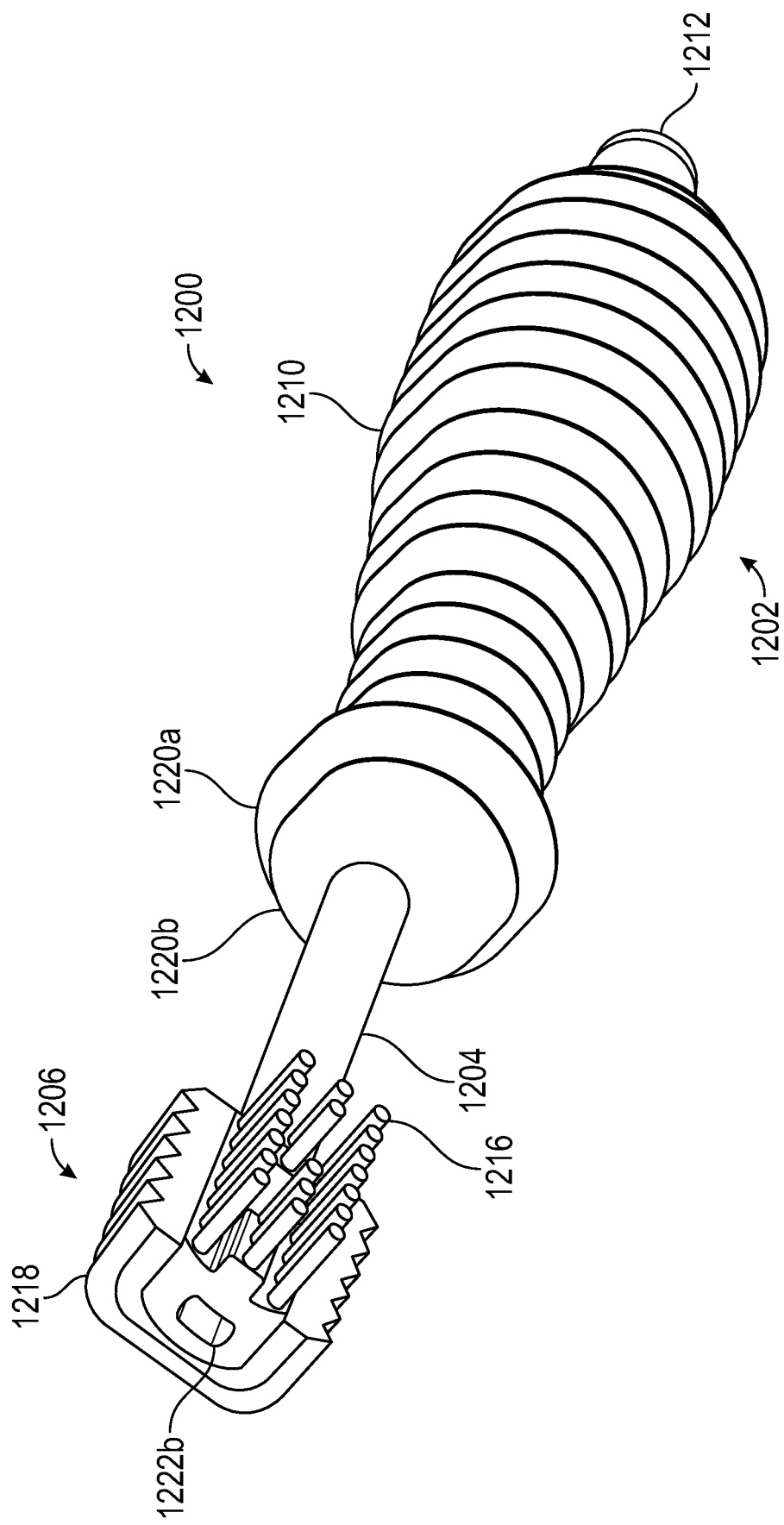
FIG. 18E is a top perspective view of the toothbrush of FIGS. 18A-18D, according to an exemplary embodiment.

As noted above, the head 1206 includes bristles 1216 and a foam section 1218. In some embodiments, the foam section 1218 is located on both the back and sides of the head 1206, as shown in FIG. 18E illustrating a top perspective view of the toothbrush 1200. In other embodiments, the foam section 1218 is located on only one of the back or sides of the toothbrush head 1206. Further, in some embodiments, the foam section 1218 is glued to the head 1206 of the toothbrush 1200, while in other embodiments the foam section 1218 is attached to the head 1206 through another mechanism (e.g., through an interference fit). As shown, in some embodiments, the foam section 1218 has ridges to aid in cleansing. In various embodiments, the head 1206 also includes one or more suction holes to provide for suction of fluids (e.g., saliva, antiseptic or other oral fluid, etc.) from the mouth of the user. The suction hole(s) are located on a top, front, and/or back of the head 1206. In the embodiment shown in FIGS. 18A-18E, the toothbrush 1200 includes a suction hole 1222a formed transversely through the center of the head 1206 and a suction hole 1222b formed on a top end of the toothbrush.

Similar to the toothbrush 900, in some embodiments, the toothbrush 1200 is manufactured using cored out injection molding. In other embodiments, the toothbrush is manufactured in separate pieces and assembled to form the completed toothbrush 1200. Additionally, the toothbrush 1200 is described herein with reference to the oral care system 1180. However, it should be understood that the toothbrush 1200 may be used with any of the oral care systems described herein. Moreover, it should further be understood that the oral care system 1180 may be used with a differently designed toothbrush, such as the toothbrush 100 or the toothbrush 900.

Figure 19A:
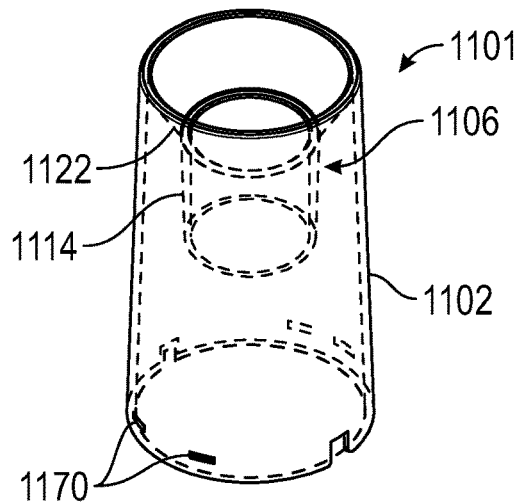
FIG. 19A is a schematic side perspective view of an oral fluid bottle of FIG. 17, according to an exemplary embodiment.
Figure 19B:
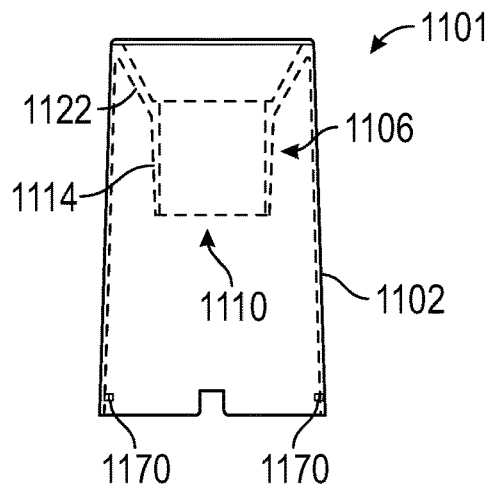
FIGS. 19B and 19C are schematic side views of the oral fluid bottle of FIG. 19A, according to an exemplary embodiment.
Figure 19C:
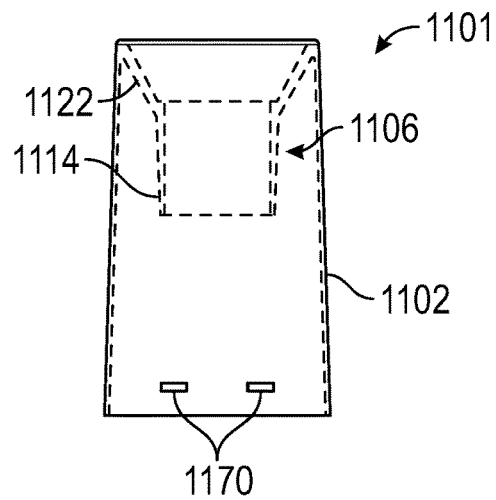

Referring now to FIGS. 19A-19C, schematic side views of the oral fluid bottle 1101 are shown, according to an exemplary embodiment. The oral fluid bottle 1101 includes a receptacle 1102 and an internal chamber 1106 defined within an interior portion of the oral fluid bottle 1101, where the internal chamber includes outlet 1110. As shown in FIGS. 19A-19C, the internal chamber 1106 includes a funnel portion 1122 that narrows to a neck portion 1114. The internal chamber 1106 thus provides a channel for receiving the spittoon straw 1400, as discussed in further detail below. Additionally, the funnel portion 1122 provides additional spill resistance to the oral fluid container 1100. In the embodiment shown, the receptacle 1102 of the oral fluid bottle 1101 is configured as a hollow, circular cylinder, though in other embodiments the receptacle 1102 has another shape (e.g., a rectangular shape). Additionally, the oral fluid bottle 1101 is configured to be relatively tall compared to the other components of the oral care system 1180 and to widen from a top of the oral fluid bottle 1101 to the bottom, which provides stability for the oral fluid bottle 1101.

The receptacle 1102 is configured to receive the cylinder solution cup 1300 through a lower portion of the receptacle 1102. As shown in FIG. 19A, the receptacle 1102 has an open bottom portion for receiving the cylinder solution cup 1300, though in other embodiments the receptacle 1102 is structured to receive the cylinder solution cup 1300 differently (e.g., include a slot for sliding in the cylinder solution cup 1300). In various embodiments, the receptacle 1102 includes apertures 1170 for locking the cylinder solution cup 1400 into the receptacle 1102. The apertures 1170 may have various arrangements on the receptacle 1102. For example, in some embodiments, the receptacle 1102 includes two sets of two apertures 1170, opposite one another, near the bottom portion of the receptacle 1102.

Figure 20A:
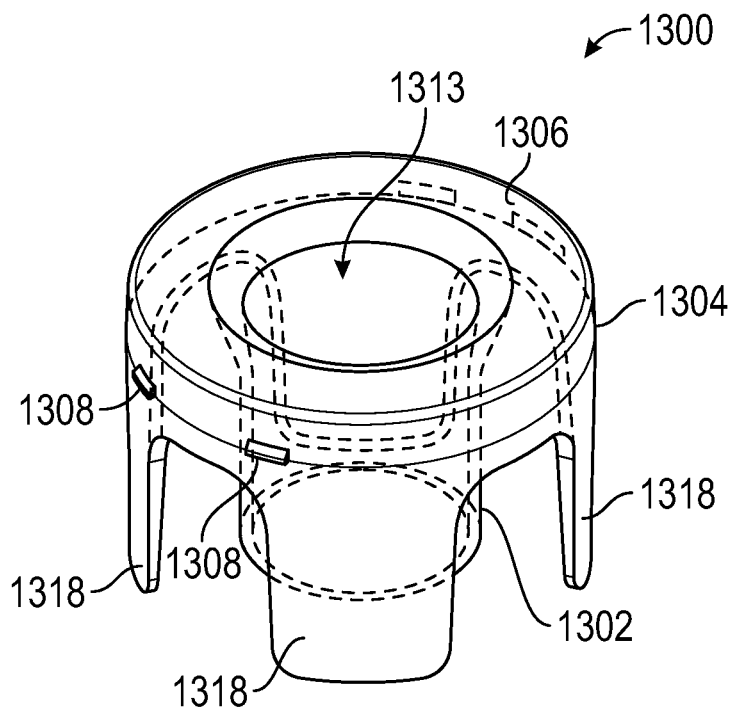
FIG. 20A is a schematic side perspective view of a cylinder solution cup configured to snap into the oral fluid bottle of FIGS. 19A-19C, according to an exemplary embodiment.
Figure 20B:
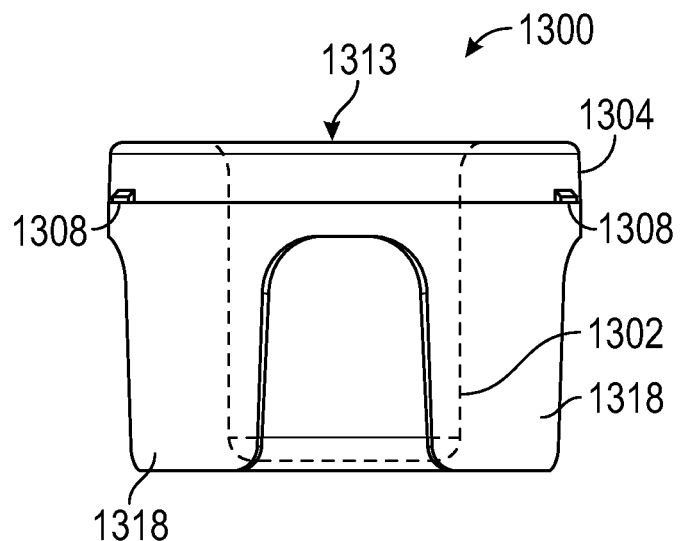
FIGS. 20B and 20C are schematic side views of the cylinder solution cup of FIGS. 20A and 20B, according to an exemplary embodiment.

FIG. 20A shows a schematic side perspective view of the cylinder solution cup 1300, and FIGS. 20B and 20B show schematic side views of the cylinder solution cup 1300, according to an exemplary embodiment. The cylinder solution cup 1300 includes a base 1302 configured to serve as a repository for an oral fluid and which receives brushing waste from a patient brushing his or her teeth. The base 1302 is configured to be wide enough to receive the end of the spittoon straw 1400, as well as deep enough that the head 1206 of the toothbrush 1200 provided in the spittoon straw 1400 can be at least partially submerged in the oral fluid contained therein, as described in further detail below. Moreover, the cylinder solution cup 1300 is configured to hold a sufficient amount of oral fluid such that when the toothbrush 1200 and spittoon straw 1400 are dipped into the oral fluid, the volume change in the oral fluid due to displacement allows the head 1206 of the toothbrush 1200 to be substantially submerged in the oral fluid while at the same time not spilling any of the oral fluid out of the top of the cup 1300. In some embodiments, the cylinder solution cup 1300 is configured to hold approximately 7.5 mL of oral fluid.

The cylinder solution cup 1300 includes a rim 1304 that defines a ledge 1306 and carries projections 1308. The projections 1308 are spaced to align with the apertures 1170 of the oral fluid bottle 1101 such that the projections 1308 can snap into the apertures 1170 to lock the cylinder solution cup 1300 into the receptacle 1102 of the oral fluid bottle 1101. Additionally, the rim 1304, and the cylinder solution cup 1300 overall, are configured such that when the projections 1308 are snapped into the apertures 1170, the receptacle 1102 of the oral fluid bottle 1101 and the rim 1304 of the cylinder solution cup 1300 can contain a liquid.

Figure 20C:
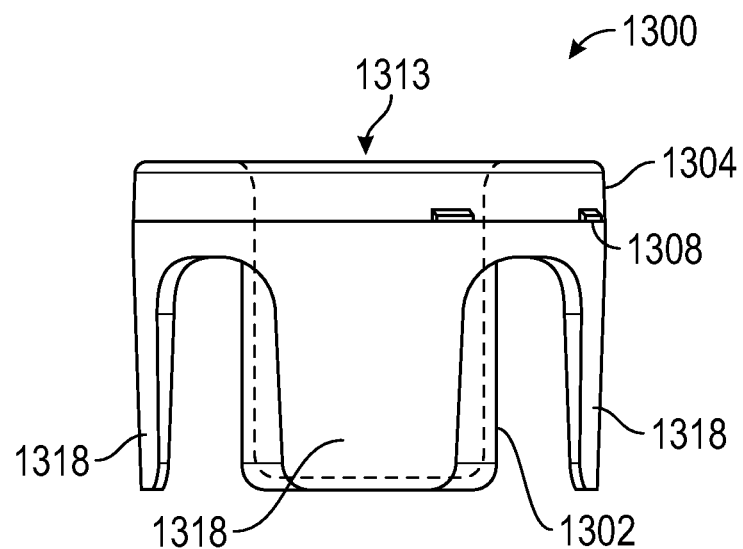

Furthermore, the cylinder solution cup includes legs 1318 defining an internal space into which the base 1302 projects. The legs 1318 are spaced apart so as to provide the cylinder solution cup 1300 and, once the cylinder solution cup 1300 is snapped into the oral fluid bottle 1101, the oral fluid container 1100 as a whole a stable base. The cylinder solution cup 1300 may include any number of legs 1318 that provide a stable base, though in the embodiment shown in FIGS. 20A-20C the cylinder solution cup 1300 has four legs 1318.

Figure 20D:
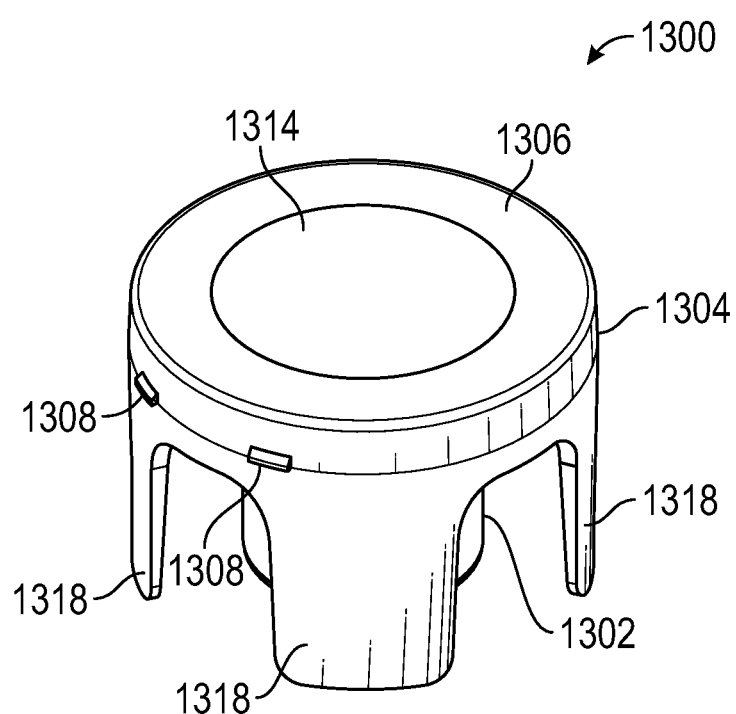
FIG. 20D is a side perspective view of the cylinder solution cup of FIGS. 20A-20C with a seal, according to an exemplary embodiment.

The rim 1304 also defines an opening 1313 at a top of the cylinder solution cup 1300 that feeds into the base 1302. In various embodiments, the opening 1313 is covered by a seal 1314, as illustrated in FIG. 20D. The seal 1314 is formed of a foil, plastic, or other frangible material that can be pierced or breached. The seal 1314 is configured to contain the oral fluid inside the base 1302 until the oral care system 1180 is to be used. However, the seal 1314 is also configured to be breached, such as by being pierced by the spittoon straw 1400 when a patient uses the oral care system 1180, as described in further detail below. After the seal 1314 has been breached or pierced, the head 1206 of the toothbrush 1200 is at least partially submerged in the oral fluid contained within the base 1302. Alternatively, in other embodiments, the opening 1313 is instead sealed through another penetrable barrier, such as a cover with a cross cut similar to the cover 1012 discussed above with respect to the cylinder solution cup 1000.

Figure 21A:
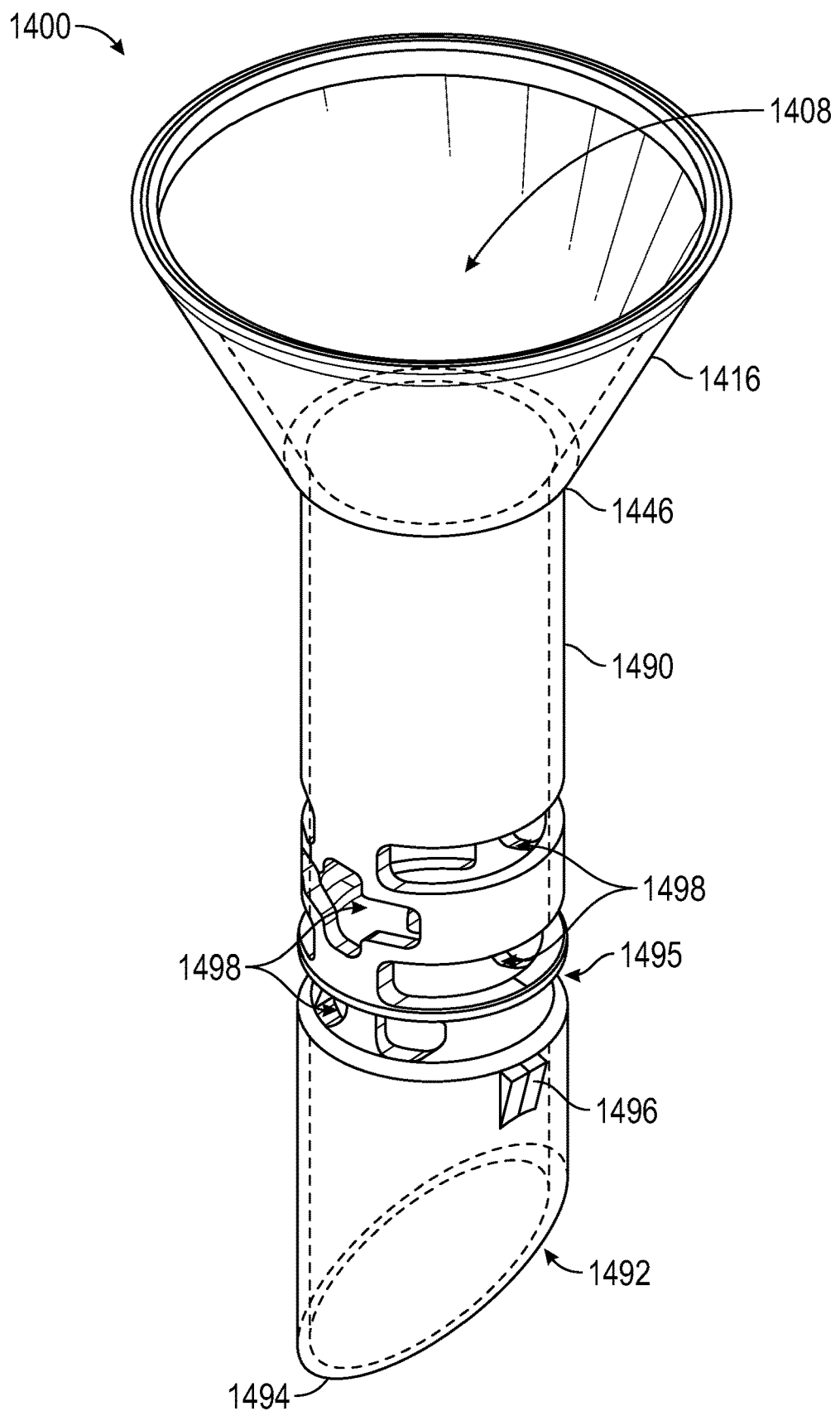
FIG. 21A is a schematic side perspective view of a spittoon straw of FIG. 17, according to an exemplary embodiment.

Referring now to FIGS. 21A, a schematic side perspective view of the spittoon straw 1400 is shown, according to an exemplary embodiment. The spittoon straw 1400 includes a funnel 1416 that connects at a base 1446 of the funnel 1416 to a tube 1490 with an opening 1492 at the end thereof. The funnel 1416 and the tube 1490 are configured to be inserted into the internal chamber 1106 of the oral fluid bottle 1101 such that the tube 1490 protrudes into the receptacle 1102. Accordingly, the spittoon straw 1400 facilitates the passage of brushing waste into an internal portion of the receptacle 1102 during or after the use of a toothbrush (e.g., toothbrush 1200) by the patient. The funnel 1416 provides a larger area for the patient to deposit the brushing waste into while brushing to minimize any mess associated with spitting into the unit dose oral fluid container 1100. The funnel 1416 and the tube 1490 then channel the brushing waste into the receptacle 1102 via an inlet 1408 of the spittoon straw 1400 and the opening 1492. Additionally, the end of the spittoon straw 1400 is cut at a diagonal, such that the plane of the opening 1492 lies at an angle relative to the axis of the straw 1400. In this way, the end of the straw at the opening 1492 comprises a leading edge that forms a cutting portion 1494 on one side. The cutting portion 1494 can be used to break or breach the seal 1314 on the cylinder solution cup 1300 snapped into the oral fluid bottle 1101.

Figure 21B:
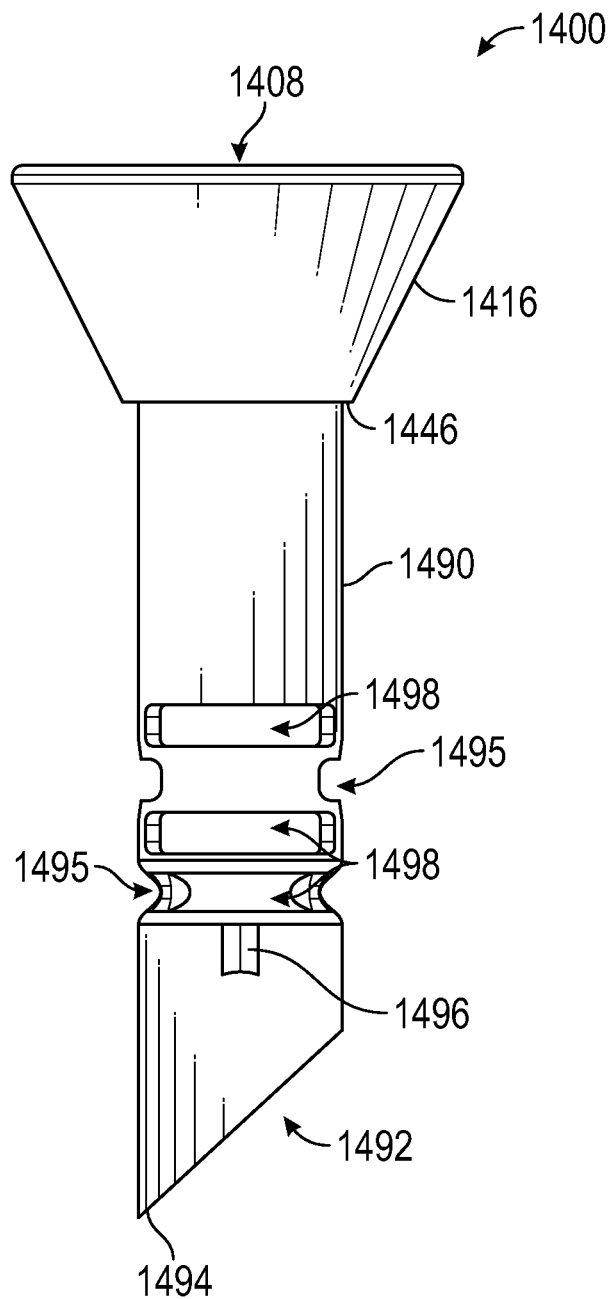
FIGS. 21B and 21C are side views of the spittoon straw of FIG. 21A, according to an exemplary embodiment.
Figure 21C:
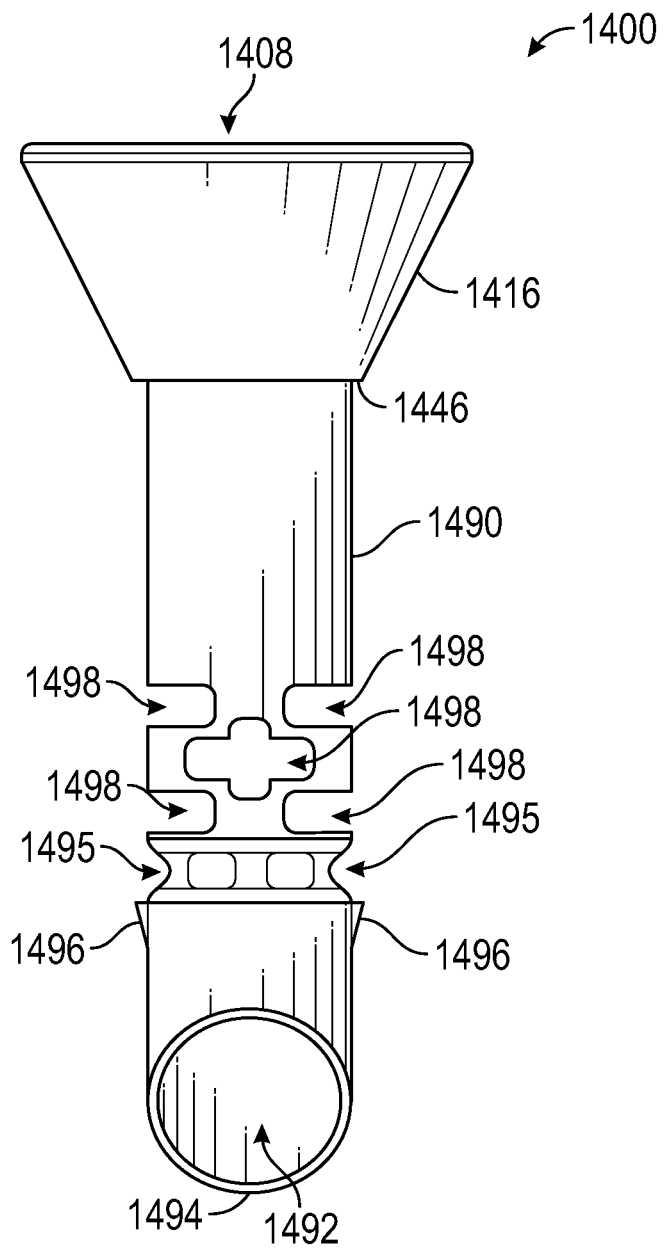

Referring now to FIGS. 21B and 21C, side views of the spittoon straw 1400 are shown, according to an exemplary embodiment. As shown in FIGS. 21B and 21C, the funnel base 1446 includes a lip such that the base 1446 is wider than the top of the tube 1490 of the spittoon straw 1400. Accordingly, the spittoon straw 1400 is configured to receive the toothbrush 1200 in a central channel of the spittoon straw 1400 formed in the funnel 1416 and the tube 1490 such that the projection seal 1220a rests on the base 1446, thereby sealing the oral care system 1180 from outside contaminants once assembled. Additionally, the tube 1490 is sized with a diameter wide enough to snugly fit the projection seal 1220b therein, further sealing the oral care system 1180 from outside contaminants. Furthermore, as shown, the tube 1490 includes an indentation 1495. The indentation 1495 is configured to rest below the head 1206 of the toothbrush 1200 such that once the toothbrush 1200 is inserted into the tube 1490, a small force must be applied to remove the toothbrush 1200 from the spittoon straw 1400.

As shown in FIGS. 21A-21C, the tube 1490 of the spittoon straw 1400 also includes projections 1496. The projections 1496 are angled such that the spittoon straw 1400 can be inserted into the internal chamber 1106 of the oral fluid bottle 1101 but, once inserted, configured to abut against the outlet 1110 of the oral fluid bottle 1101 to prevent spittoon straw 1400 from being pulled out from the internal chamber 1106. As such, the projections 1496 prevent the spittoon straw 1400 from be pulled out of the oral fluid container 1100 once inserted. In the embodiment shown in FIGS. 21A-21C, the spittoon straw 1400 includes two projections 1496, though in other embodiments, the spittoon straw 1400 may include more projections 1496. Alternatively, in other embodiments, the spittoon straw 1400, the oral fluid bottle 1101, and/or the cylinder solution cup 1300 include a different mechanism for preventing the spittoon straw 1400 from sliding out of the oral fluid bottle 1101. In one example, the spittoon straw 1400 includes projections 1496 further down the length of the tube 1490, and the top of the cylinder solution cup 1300 includes notches that engage with the projections 1496. Accordingly, once the spittoon straw 1400 is pushed into the cup 1300, the engagement between the projections 1496 and the notches prevent the spittoon straw 1400 from being subsequently pulled out from the cup 1300. In another example, the funnel 1416 includes projections, and the top of the oral fluid bottle 1101 includes notches that engage with the projections such that once the spittoon straw 1400 is pushed far enough into the oral fluid bottle 1101, the notches engage with the projections and the spittoon straw 1400 cannot subsequently be pulled back beyond the notches.

Furthermore, the spittoon straw 1400 includes apertures 1498 formed into a side wall of the tube 1490 of the spittoon straw 1400. The apertures 1498 allow the oral fluid container 1100, including the oral fluid bottle 1101, cylinder solution cup 1300, and spittoon straw 1400, to be spill-resistant. For example, when the oral fluid container 1100 is tipped, liquids contained within the receptacle 1102 (e.g., unused oral fluid, brushing waste) may flow into the tube 1490 of the spittoon straw but subsequently flow out through the apertures 1498 in the side wall of the tube 1490 and back into the receptacle 1102. The apertures 1498 are designed to provide a maximum amount of flow out of the tube 1490 without compromising the structural integrity of the tube 1490.

Referring back to FIG. 17, the assembled oral care system 1180 is shown. Accordingly, the cylinder solution cup 1300 has been snapped into the oral fluid bottle 1101 such that the projections 1308 of the cylinder solution cup 1300 fit into the apertures 1170 of the oral fluid bottle 1101. Additionally, the spittoon straw 1400 has been inserted into the internal chamber 1106 of the oral fluid bottle 1101 such that the projections 1496 prevent the spittoon straw 1400 from being pulled out of the oral fluid container 1100. As shown, in the embodiment of FIG. 17, the components of the oral fluid container 1100 (i.e., the oral fluid bottle 1101, the cylinder solution cup 1300, and the spittoon straw 1400) are configured to have circular cross sections, though in other embodiments, the components may have different cross sections (e.g., elliptical, oblong).

The toothbrush 1200 has also been inserted into the tube 1490 of the spittoon straw 1400 in FIG. 17. The head 1206 of the toothbrush 1200 is positioned below the indentation 1495 such that the indentation 1495 holds the toothbrush 1200 within the spittoon straw 1400 and a small force must be applied to remove the toothbrush 1200 from the spittoon straw 1400. Accordingly, the projection seal 1220a rests on the base 1446 of the spittoon straw 1400, and the projection seal 1220b sits inside the tube 1490. Together, the projection seals 1220a and 1220b seal the interior of the oral care system 1180 from outside contaminants. Additionally, the projection seal 1220a resting on the base 1446 prevents the toothbrush 1200 from sliding completely into the tube 1490 and into the receptacle 1102. Similarly, the projection seal 1220b fits snugly into the tube 1490 such that the circumference of the projection seal 1220b abuts the wall of the tube 1490, further sealing the oral fluid container 1100. Furthermore, the fact that the projections 1220 are offset from the center of the toothbrush 1200 allows the toothbrush 1200 to be inserted into the spittoon straw 1400 without crushing the bristles 1216 of the toothbrush head 1206.

In some embodiments, the oral care system 1180 is packaged as a pre-assembled unit as shown in FIG. 17. In other embodiments, the oral care system 1180 is packaged as separate components (e.g., the oral fluid bottle 1101, toothbrush 1200, cylinder solution cup 1300, and spittoon straw 1400 are packaged separately) such that a user, such as a care provider or a patient, must assemble the oral care system 1180. Additionally, the components of the oral care system 1180 are manufactured from any type of appropriate spill-resistant and sanitary materials. For example, in some embodiments, the seal 1314 is made from a polyethylene film, and the cylinder solution cup is a polyethylene cup. Additionally, the oral fluid bottle 1101 and the spittoon straw are made of polypropylene.

Figure 22A:
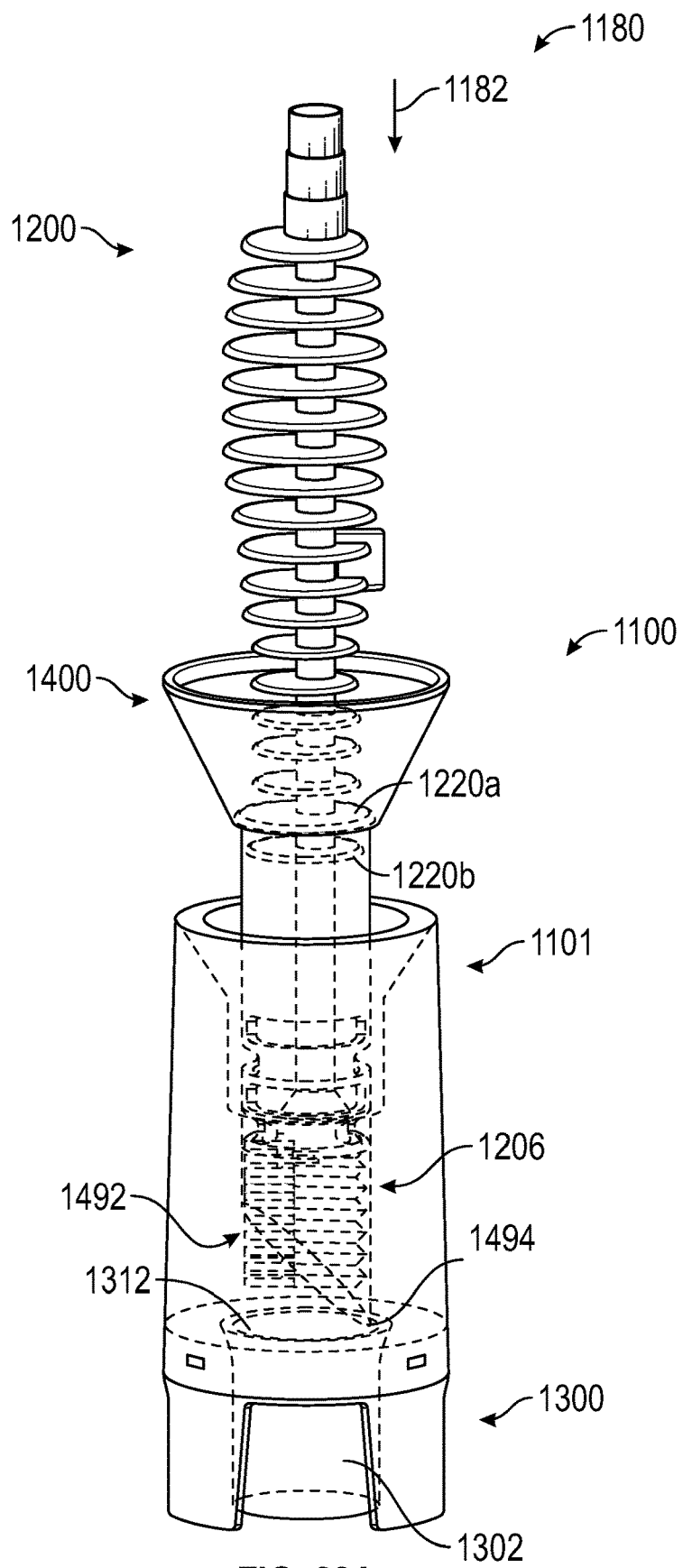
FIGS. 22A-22H depict steps of using an oral care system including the toothbrush of FIGS. 18A-18E, the oral fluid bottle of FIGS. 19A-19C, the cylinder solution cup of FIGS. 20A-20C, and the spittoon straw of FIGS. 21A-21C, according to an exemplary embodiment.
Figure 22B:
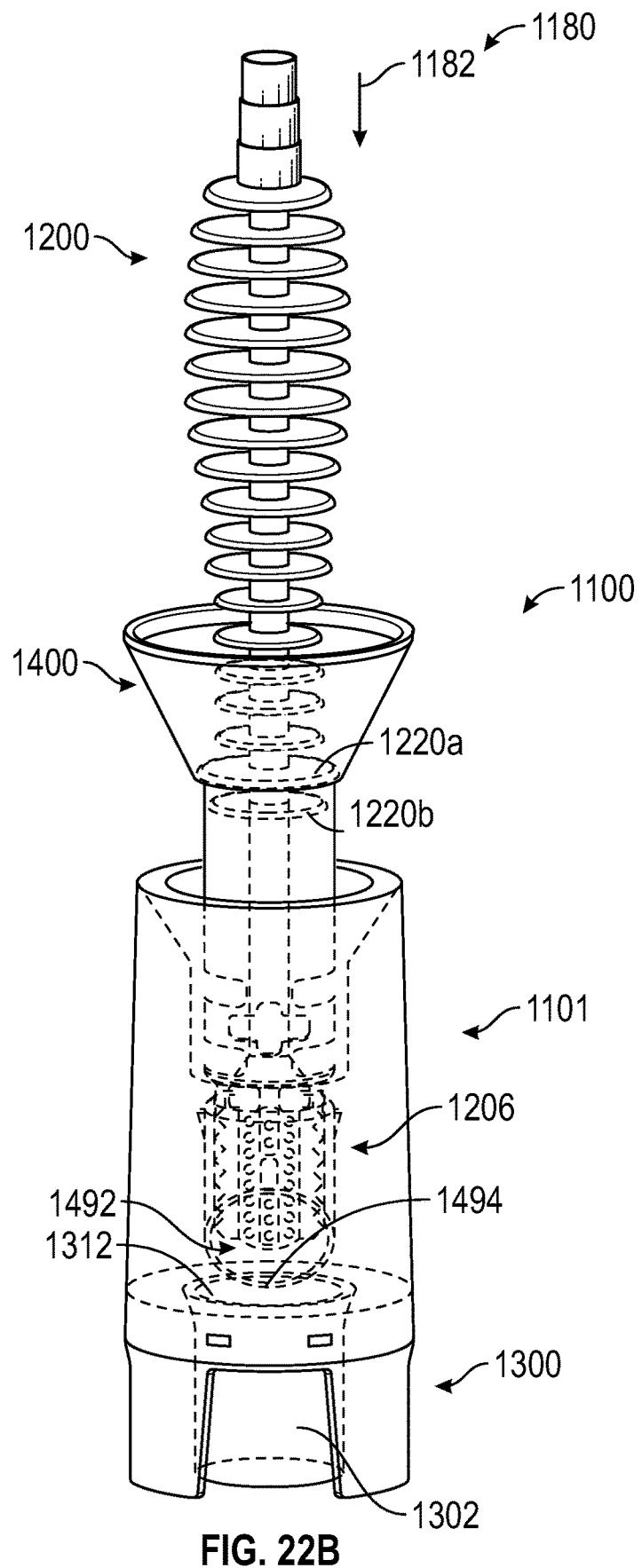

Referring now to FIGS. 22A-22H, side views of the oral care system 1180 are shown during steps of use. To begin with, FIGS. 22A and 22B depict side views of the assembled oral care system 1180 before use. As shown, the point 1494 of the spittoon straw 1400 rests proximal the seal 1314 of the cylinder solution cup 1300. To use the oral care system 1180, a patient or care provider thus pushes on the toothbrush 1200 and/or the spittoon straw 1400 as depicted by arrow 1182 until the point 1494 of the spittoon straw 1400 breaches the seal 1314. In some embodiments, the spittoon straw 1400 can be moved approximately 0.64 cm (0.25 inches) within the receptacle 1102. Accordingly, the patient or care provider can move the spittoon straw 1400 in a first direction and subsequently push the spittoon straw 1400 in an opposite direction towards the seal 1314 to facilitate breaching, such as breaking, of the seal 1314.

Figure 22C:
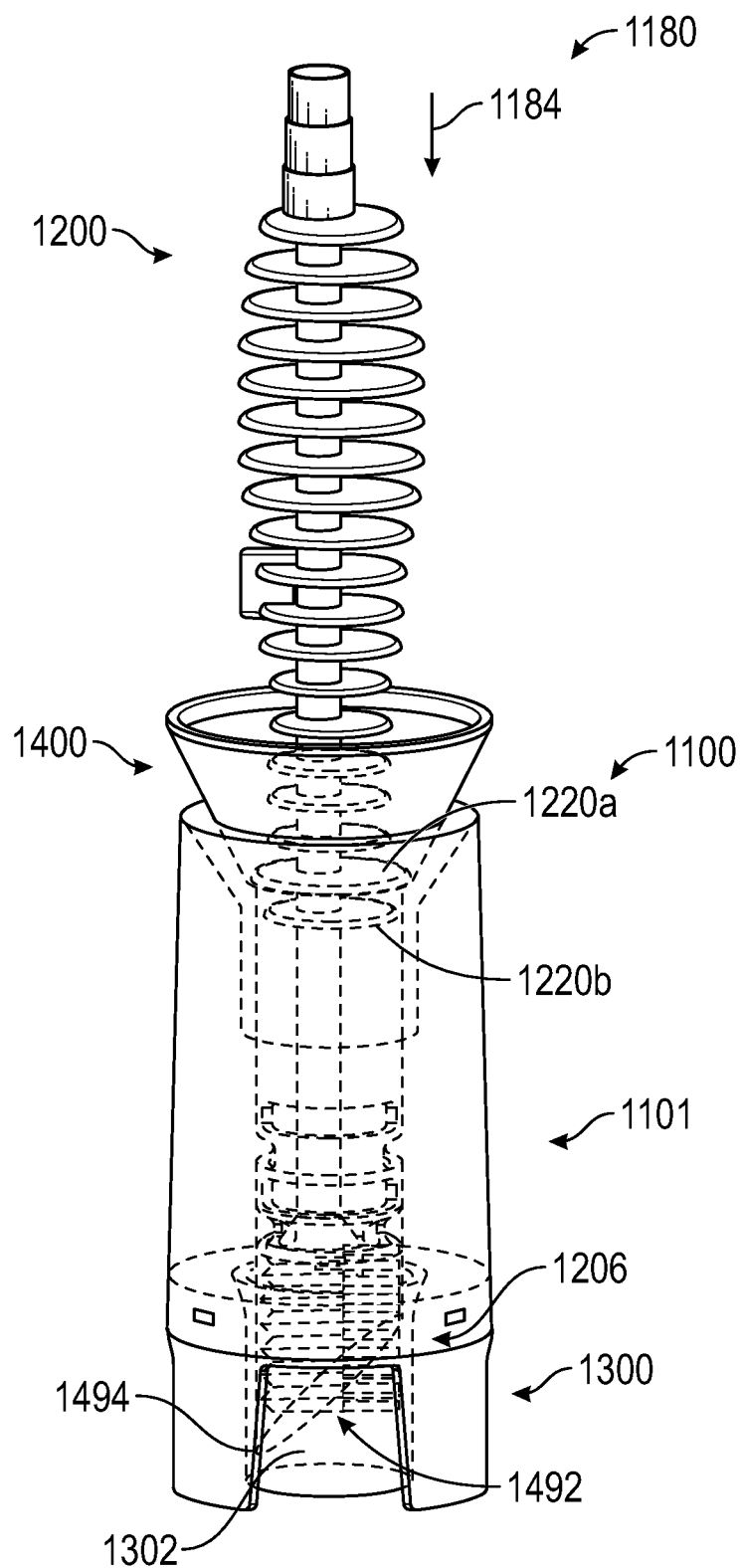
Figure 22D:
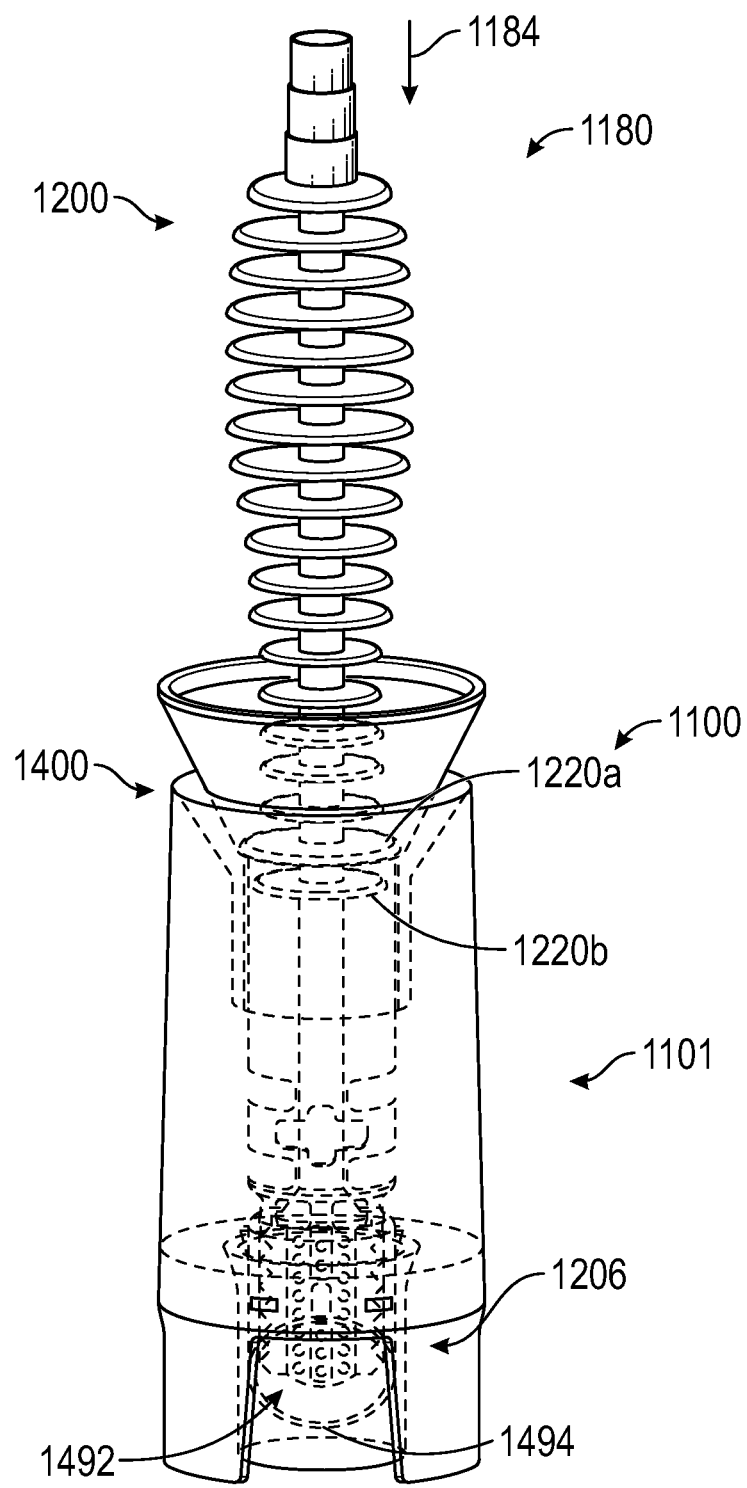

The patient or care provider then continues to press the toothbrush 1200 and/or the spittoon straw 1400 in a direction depicted by arrow 1184 such that the opening 1492 of the spittoon straw 1400 and the head 1206 of the toothbrush 1200 become substantially submerged in the oral fluid contained within the base 1302 of the cylinder solution cup 1300. The patient or care provider presses until the point 1494 of the spittoon straw 1400 reaches proximal the bottom of the cylinder solution cup 1300 as shown in FIGS. 22C and 22D. Doing so ensures that the head 1206 of the toothbrush 1200 is substantially submerged in the oral fluid.

Figures 22E, 22F:
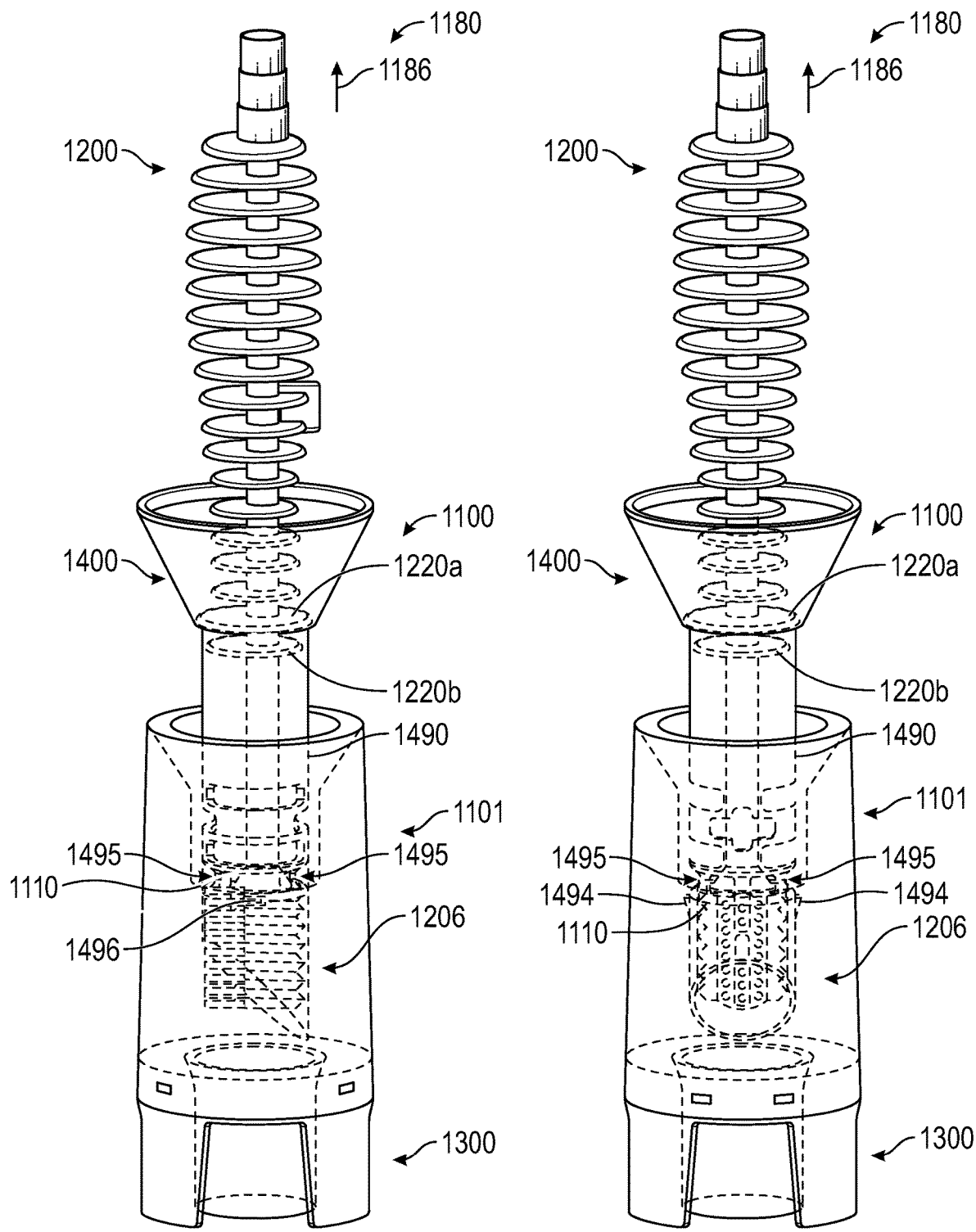
Figure 22G:
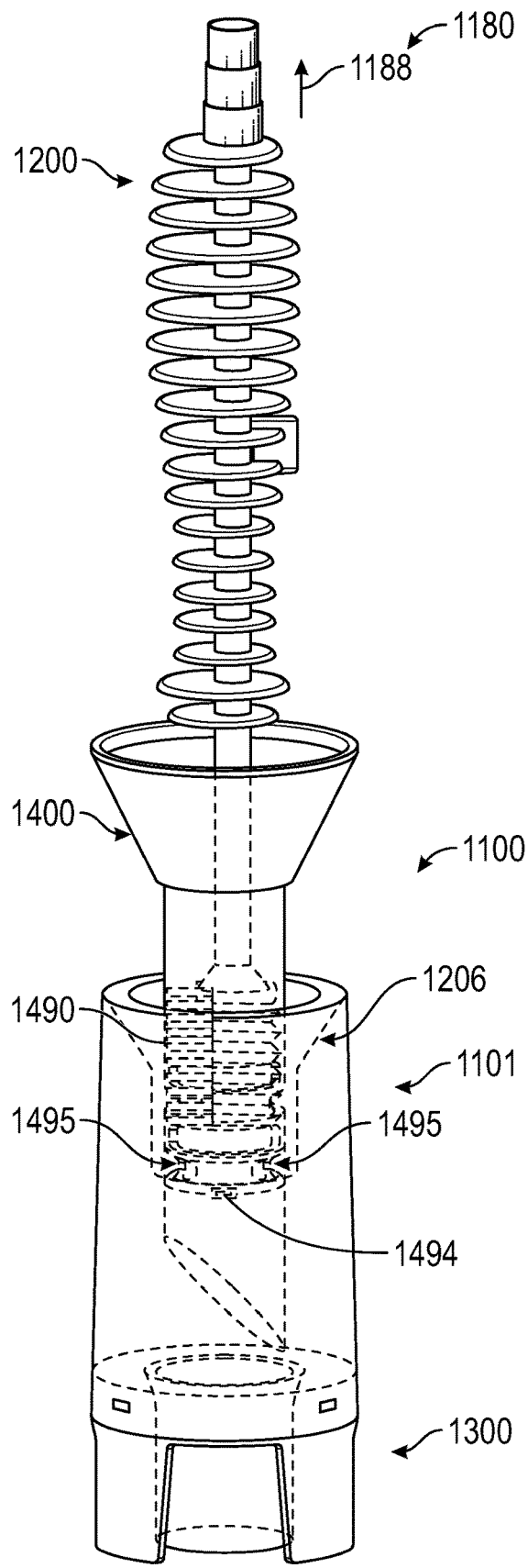
Figure 22H:
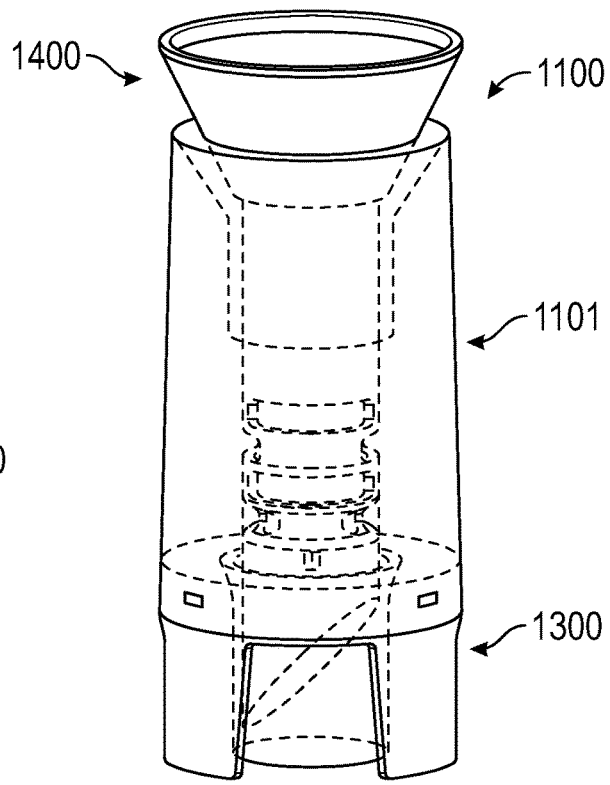

Once the toothbrush head 1206 is substantially submerged in the oral fluid, the patient or care provider pulls on the toothbrush 1200 and/or the spittoon straw 1400 in a direction depicted by arrow 1186. Doing so withdraws the spittoon straw 1400 and the toothbrush 1200 contained therein. The spittoon straw 1400 continues to be withdrawn until the projections 1496 on the tube 1490 of the spittoon straw 1400 contact the outlet 1110 of the oral fluid container, as shown in FIGS. 22E and 22F. The projections 1496 thus prevent the spittoon straw 1400 from being withdrawn further. At this point, the patient or care provider continues to pull the toothbrush 1200 in a direction depicted by arrow 1188 until the head 1206 of the toothbrush 1200 slides past the indentation 1495 and out of the spittoon straw 1400, as shown in FIG. 22G. In some embodiments, the tube 1490 is configured to squeeze excess oral fluid from the head 1206 of the toothbrush 1200 as the toothbrush 1200 is pulled out of the spittoon straw 1400. Once the toothbrush 1200 is removed from the oral care system 1180, the spittoon straw 1400 falls back into the oral fluid bottle 1101 and/or into the cylinder solution cup 1300 as shown in FIG. 22H. As such, a care provider can easily check that the patient has used the oral care system 1180 by looking to see whether the spittoon straw 1400 is in its original position with respect to the oral fluid container 1100, or whether it has fallen into the oral fluid bottle as shown in FIG. 22H indicating use.

Once the patient has pulled the toothbrush 1200 out of the oral care system 1180, the patient can use the toothbrush 1200 in a standard fashion to brush the patient's teeth. During or after brushing, the patient spits into the funnel 1416 of the spittoon straw 1400 to remove oral fluid from the patient's mouth. When the patient has finished the oral care treatment, the oral care system 1180 is to be disposed. In some arrangements, the patient reinserts the toothbrush 1200 into the tube 1490 of the spittoon straw 1400 before disposing of the oral care system 1180.

Any of the oral care systems described herein, or another system combining a toothbrush (e.g., toothbrush 100, toothbrush 900, or toothbrush 1200) with a unit dose oral fluid container (e.g., oral fluid container 200, 400, 500, 600, or 700; oral fluid container 800 including the oral fluid bottle 801 and cylinder solution cup 1000; or oral fluid container 1100 including the oral fluid bottle 1101, cylinder solution cup 1300, and spittoon straw 1400), may be packaged individually or may be packaged as a kit including three or four oral care systems. Therefore, a care provider can leave a kit for a patient in the morning, and the patient will have the correct number of oral care systems that the patient should use in a given day. The care provider can also check the oral care systems for broken seals, brushing waste, or, in the case of the oral care system including the spittoon straw, that the spittoon straw is in the used position wherein the spittoon straw has fallen into the oral fluid container to verify patient compliance in following a preferred oral care plan. In some embodiments, the packaging may be designed with a small footprint for storage on a bedside table in a hospital room. In certain embodiments, the packaging further includes an element to cover or protect the funnel opening of the oral fluid container to minimize unwanted particles or materials from falling into the device and onto the toothbrush.

The construction and arrangement of the elements of the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and assemblies may be constructed from any of a wide variety of materials that provide sufficient strength or durability, in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

What is claimed is:

1. A method of using an oral care system, comprising:
    obtaining an oral care system, the oral care system comprising:
        a container defining an interior portion and comprising:
            a repository provided within the interior portion and configured to hold a fluid;
            a barrier configured to maintain the fluid separate from the interior portion, wherein the barrier is configured to be breached to expose the interior portion to the fluid; and
            a tube configured to slide into the interior portion of the container, the tube comprising a distal end configured to breach the barrier; and
        a toothbrush held by the tube; and
    moving the tube in a first direction toward the repository; and
    breaching the barrier by the distal end of the tube to expose the interior portion of the container to the fluid.

2. The method of claim 1, further comprising continuing to move the tube in the first direction to expose a distal end of the toothbrush to the fluid in the repository.

3. The method of claim 2, further comprising moving the tube in a direction opposite the first direction to remove the distal end of the toothbrush from the fluid.

4. The method of claim 3, further comprising removing the toothbrush from the tube to perform an oral treatment.

5. The method of claim 4, wherein the tube is configured such that when the toothbrush is removed from the tube, excess solution is removed from the toothbrush.

6. The method of claim 1, wherein movement of the tube is caused by movement of the toothbrush.

7. The method of claim 1, further comprising coupling a suction device to a suction port on the toothbrush.

8. The method of claim 7, further comprising coving a suction hole in a handle of the toothbrush to generate suction in the toothbrush.

9. The method of claim 1, wherein the repository is a solution cup configured to hold the fluid therein, and wherein the barrier is positioned over a top of the solution cup, and
    wherein breaching the barrier comprises moving the distal end of the tube through the barrier over the top of the solution cup.

10. The method of claim 1, wherein the distal end of the tube comprises a cutting edge formed by the distal end of the tube being cut at an angle relative to a central axis of the tube, for breaching the barrier.

11. The method of claim 1, wherein the container further comprises a spittoon straw comprising a funnel portion and the tube connected to a base of the funnel portion.

12. The method of claim 11, further comprising collecting brushing waste in the funnel portion and retaining the brushing waste in a second portion of the container, separate from the repository.

13. The method of claim 1, further comprising moving the container in any orientation, and wherein the tube comprises at least one aperture formed in a side wall of the tube, the at least one aperture configured to allow the fluids to pass from the tube into the interior portion to maintain the fluids within the interior portion of the container independent of the orientation of the container.

14. The method of claim 1, further comprising sealing the interior portion from an exterior of the container when the toothbrush is inserted into the interior portion, wherein the toothbrush comprises a handle and a plurality of projections formed on the handle and at least one of the projections is configured to seal the interior portion from an exterior of the container.

* * * * *